United States Patent
Iwakiri et al.

(10) Patent No.: US 8,532,262 B2
(45) Date of Patent: Sep. 10, 2013

(54) RADIOGRAPHIC IMAGE CAPTURING SYSTEM

(75) Inventors: Naoto Iwakiri, Kanagawa (JP); Naoyuki Nishino, Kanagawa (JP); Yasunori Ohta, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 478 days.

(21) Appl. No.: 12/929,541

(22) Filed: Jan. 31, 2011

(65) Prior Publication Data
US 2011/0228904 A1    Sep. 22, 2011

(30) Foreign Application Priority Data

Mar. 17, 2010  (JP) ................................. 2010-061099
Dec. 15, 2010  (JP) ................................. 2010-279683

(51) Int. Cl.
*H05G 1/44* (2006.01)
*H05G 1/64* (2006.01)
*H01L 27/144* (2006.01)

(52) U.S. Cl.
USPC ...................... 378/108; 378/98.8; 250/370.09

(58) Field of Classification Search
USPC ................... 378/4–20, 62, 91, 98, 98.8, 108, 378/204, 210; 250/370.01, 370.08, 370.09
See application file for complete search history.

(56) References Cited

FOREIGN PATENT DOCUMENTS

| JP | 6-189948 A | 7/1994 |
|----|------------|--------|
| JP | 11-128214 A | 5/1999 |
| JP | 2005-323673 A | 11/2005 |
| JP | 2007-007243 A | 1/2007 |
| JP | 2009-032854 A | 2/2009 |
| JP | 2009-212389 A | 9/2009 |

*Primary Examiner* — Anastasia Midkiff
(74) *Attorney, Agent, or Firm* — SOLARIS Intellectual Property Group, PLLC

(57) ABSTRACT

A radiographic image capture system includes a radiation detector, a radiation source, a generator, and a controller. The radiation detector includes plural pixels that generate electrical charges upon irradiation with radiation and that accumulate the electrical charges. The radiation source irradiates radiation onto the radiation detector. The generator reads the respective electrical charges accumulated in each of the pixels as electrical signals and generates image data. The controller causes the generator to read the electrical charges accumulated in each of the pixels at a specific frame rate in cases where continuous fluoroscopic imaging is performed, and, in a case in which a specific condition is satisfied, causes the radiation source to reduce the radiation amount being irradiated and causes the generator to perform thinned reading to read out the pixels one section at a time while extending the reading cycle of the electrical charges for each pixel.

12 Claims, 17 Drawing Sheets

RADIOGRAPHIC IMAGE CAPTURING SYSTEM

CROSS-REFERENCE TO RELATED APPLICATION

This application claims priority under 35 USC 119 from Japanese Patent Applications No. 2010-061099 filed on Mar. 17, 2010, and No. 2010-279683 filed on Dec. 15, 2010, the disclosures of which are incorporated by reference herein.

BACKGROUND OF THE INVENTION

Field of the Invention

The present invention relates to a radiographic image capturing system, and in particular, to a radiographic image capturing system that can carry out fluoroscopic imaging in which the capturing of radiographic images is carried out continuously.

Radiation detectors such as flat panel detectors (FPDs), in which a radiation-sensitive layer is disposed on a thin film transistor (TFT) active matrix substrate and that can convert radiation directly into digital data have been put into practice in recent years. Portable radiographic image capturing devices (hereinafter also called "electronic cassettes"), that capture radiographic images expressed by irradiated radiation by using the radiation detector, are being put into practice. As compared with a radiographic image capturing device that uses a conventional X-ray film or imaging plate, a radiographic image capturing device that uses the radiation detector has the advantages that images can be confirmed immediately, and fluoroscopic imaging (video image capturing), in which the capturing of radiographic images is carried out continuously, also can be carried out. As methods of converting radiation at the radiation detector, there are an indirect conversion method that, after converting radiation into light at a scintillator, converts the light into charges at a semiconductor layer of photodiodes or the like, and a direct conversion method that converts radiation into charges at a semiconductor layer of amorphous selenium or the like, and the like. There exist various types of materials that can be used at the semiconductor layer in these respective methods.

As a technique related to such fluoroscopic imaging, Japanese Patent Application Laid-Open (JP-A) No. 2007-7243 discloses a technique for raising reading speed by performing thinned scanning by scanning every 1 in 4 line scan line, every 1 in 9 scan line, or every 1 in 16 scan line.

JP-A No. 11-128214 discloses a technique for raising the reading speed by dividing the pixels of an FPD into pixel blocks of 4 pixels each, and reading each of the element blocks at one time.

Furthermore, JP-A No. 6-189948 discloses a technique in which even number fields and odd number fields are alternately read by interlace scanning, and reading is interrupted when the time for reading is reached during X-ray irradiation, and reading is restarted when X-ray irradiation has ended.

However, exposure to patients is increased by fluoroscopic imaging (video image capturing). Therefore, consideration could be given to dropping the radiation irradiation amount per unit of time when the irradiation amount approaches a preset permitted irradiation amount or X-ray irradiation permitted duration.

Due to dropping the radiation irradiation amount per unit of time the irradiation amount of radiation irradiated onto a radiation detector also falls, and the reading cycle needs to be reduced or otherwise the capture of fluoroscopic images would become difficult. However, smooth fluoroscopic images may not be obtained due to the reduced reading cycle.

Techniques disclosed in JP-A No. 2007-7243 and JP-A No. 11-128214 are techniques for raising reading speed, and when the radiation irradiation amount per unit of time is reduced, the irradiation amount of radiation irradiated onto the radiation detector also falls. Accordingly, the quality of radiographic images captured reduces, and fluoroscopic imaging will be difficult.

In the technique of JP-A No. 6-189948, since image reading is halted in the irradiation period of radiation, smooth fluoroscopic images cannot be obtained, and there is a risk that an image is missed of an important timing.

SUMMARY

The present invention is made in consideration of the above circumstances, and provides a radiographic image capture system that can capture smooth fluoroscopic images even in cases in which the radiation irradiation amount being irradiated has been reduced.

A first aspect of the present invention is a radiographic image capture system including: a radiation detector including plural pixels that generate electrical charges upon irradiation with radiation and that accumulate the electrical charges; a radiation source that irradiates radiation onto the radiation detector; a generator that reads the respective electrical charges that have been accumulated in each of the pixels as electrical signals and generates image data expressing a radiographic image based on the read electrical signals; and a controller that causes the generator to read the electrical charges that have been accumulated in each of the pixels at a specific frame rate in cases where continuous fluoroscopic imaging is performed to capture radiographic images, and, in a case in which a specific condition is satisfied, causes the radiation source to reduce the radiation amount being irradiated and causes the generator to perform thinned reading to read out the plural pixels one section at a time while extending the reading cycle of the electrical charges for each pixel.

According to the radiographic image capture system of this aspect, smooth fluoroscopic images can be captured even in cases in which the radiation irradiation amount has been reduced.

In the above aspect, configuration may be made such that the controller extends the reading cycle of the electrical charges for each of the pixels corresponding to an amount by which the radiation amount being irradiated is reduced.

In the above aspect, configuration may be made such that in a case in which the specific condition is satisfied, the controller causes the radiation source to reduce the radiation amount for irradiation to 1/M, wherein M is an integer of 2 or above, times the previous value and causes the generator to perform thinned reading of the plural pixels one section at a time divided across N times, wherein N is an integer of M or above.

In the above aspect, configuration may be made such that the method of thinned reading is an interlaced scanning method.

In the above aspect, configuration may be made such that the controller causes the generator to perform thinned reading at the specific frame rate.

In the above aspect, configuration may be made such that in a case in which the specific condition is satisfied, the controller reduces the radiation amount for irradiation by performing at least one of: reducing a radiation amount per unit time for irradiation, shortening the irradiation period in cases in which radiation is irradiated in a pulse mode, or reducing a number of times of irradiation in cases in which radiation is irradiated in a pulse mode.

In the above aspect, configuration may be made such that the generator further includes an amplifier that amplifies electrical signals read from the radiation detector, and the controller increases the gain of the amplifier in a case in which the specific condition is satisfied.

In the above aspect, configuration may be made such that the specific condition is that radiation has been irradiated from the radiation source in a specific permitted amount or for a specific permitted irradiation duration.

In the above aspect, configuration may be made such that the radiographic image capture system further includes a receiver that receives an instruction to change a reading mode, wherein the specific condition is that an instruction to change the reading mode has been received by the receiver.

In the above aspect, the radiation detector may be configured by stacking a fluorescent material layer that generates light due to being irradiated with radiation and a substrate on which a photoelectric conversion element is formed, in which the photoelectric conversion element converting the light generated by the fluorescent material layer into electric charge.

The fluorescent material layer may include CsI.

The radiation detector may be configured to be irradiated with radiation from a side at which the substrate is disposed.

According to the above configurations, smooth fluoroscopic images can be captured even in cases in which the radiation irradiation amount has been reduced.

BRIEF DESCRIPTION OF THE DRAWINGS

Exemplary embodiments of the present invention will be described in detail based on the following figures, wherein.

DETAILED DESCRIPTION

Exemplary embodiments of the present invention are described in detail hereinafter with reference to the drawings. Note that, here, description is given of examples of a case in which the present invention is applied to a radiology information system that is a system that all-inclusively manages information that is handled in the radiology department of a hospital.

Figure 1:
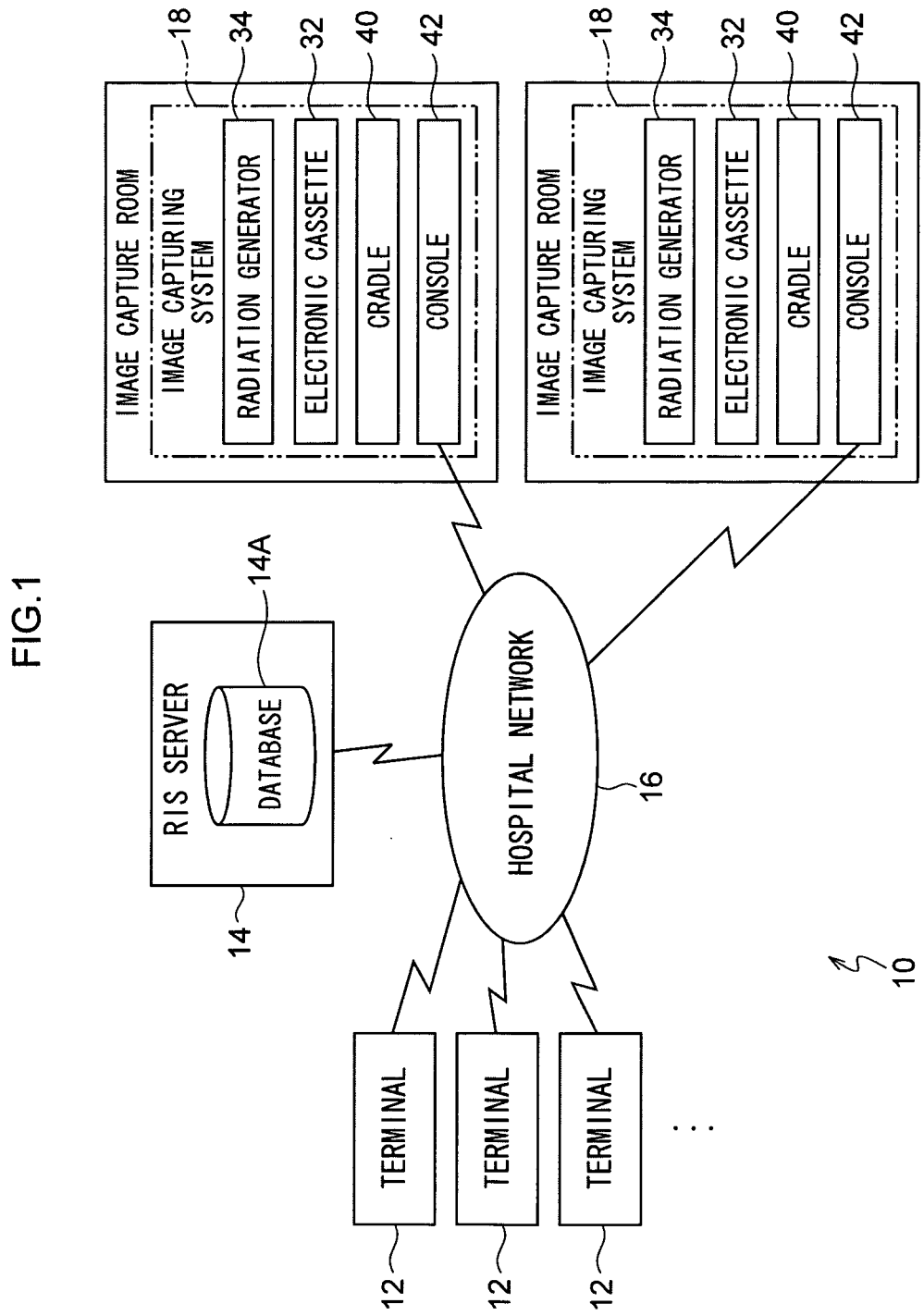
FIG. 1 is a block diagram showing the structure of a radiology information system relating to an exemplary embodiment.

Firstly, a configuration of a radiology information system 10 (which will be called "the RIS 10 below) of the present embodiment will be described in reference to FIG. 1.

The RIS 10 is a system for managing information such as medical service appointments and diagnostic records in a radiology department and configures part of a hospital information system (HIS).

The RIS 10 includes plural image capture request terminals 12 (which will be called "the terminals 12 below), RIS server 14 and radiographic image capturing systems 18 (hereinafter, referred to as "capturing systems") installed in individual radiographic image capturing rooms (or operating rooms) in a hospital being connected to a hospital network 16 that is structured by a wired or wireless local area network (LAN). The RIS 10 serves as part of the HIS that is disposed in the same hospital, and an HIS server (not shown) that manages the entire HIS is also connected to the hospital network 16.

The terminals 12 are devices for doctors or radiologic technologists to input/browse diagnostic information and facility reservations, and requests to capture radiographic images or image capture reservations are also performed from the terminals 12. Each of the terminals 12 is configured by a personal computer equipped with a display device, and the terminals 12 are connected by the hospital network 16 to the RIS server 14 so as to be capable of communicating with each other.

The RIS server 14 receives the image capture requests from the terminals 12, manages radiographic image capture schedules in the image capturing systems 18, and includes a database 14A.

The database 14A stores information (data) relating to a patient, such as attribute information (name, sex, date of birth, age, blood type, weight, patient ID (identification) and the like) of the patient, medical history, consultation history, and radiographic images captured in the past.

The image capturing systems 18 capture radiographic images by operation of the doctors or radiologic technologists in response to an instruction from the RIS server 14. Each of the capturing systems 18 is equipped with a radiation generator 34 that irradiates a subject with radiation indicated by X in the drawings (hereinafter referred to as "radiation X", see also FIG. 3) from a radiation source 130 (see also FIG. 2) of a radiation amount corresponding to image capture conditions, an electronic cassette 32 that includes a radiation detector 60 (see also FIG. 3) that absorbs the radiation X that has been transmitted through an image capture area of the patient and generates charges, and generates image information representing radiographic image information (data) based on the generated charge amount, a cradle 40 that charges a battery built into the electronic cassette 32, and a console 42 that controls the electronic cassette 32, the radiation generator 34, and the cradle 40.

Figure 2:
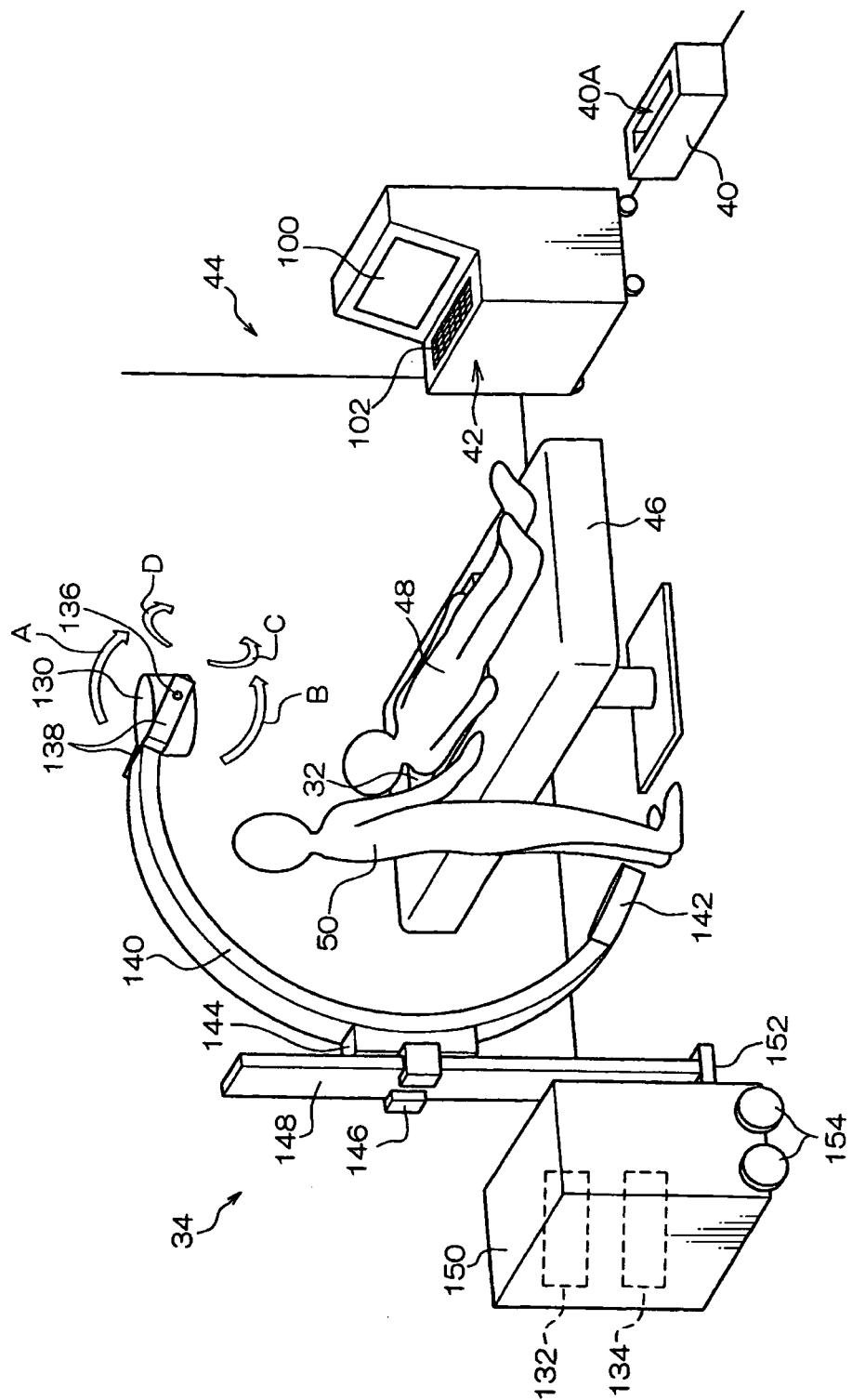
FIG. 2 is a perspective view showing an example of the state of placement of respective devices in a radiographic image capturing room of a radiographic image capturing system relating to the exemplary embodiment, and the structure of a radiation generator.

FIG. 2 shows an example of the arrangements of the image capturing systems 18 in an radiographic image capturing room 44 and a configuration of the radiation generator 34 according to the present exemplary embodiment.

In the image capturing system 18, the console 42 is mutually connected to the radiation generator 34 by a cable such that these devices transmit and receive various types of information (data) by wired communication, but in FIG. 2, the cables that interconnect these devices are omitted. Further, the electronic cassette 32 and the console 42 may transmit and receive various types of information (data) by wired or wireless communication.

The radiation generator 34 relating to the present exemplary embodiment has a C arm 140. The radiation source 130 that emits radiation X is provided at one end of the C arm 140. An attachment structure 142, to and from which the electronic cassette 32 can be attached and removed, is provided at the other end of the C arm 140. Note that FIG. 2 shows a state in which the electronic cassette 32 is removed from the attachment structure 142 and is provided between a bed 46, that is provided at the substantially central portion of the radiographic image capturing room 44, and a subject (patient) 48 who is lying on the bed 46.

The radiation source 130 is disposed at one end of the C arm 140 via a supporting shaft 136 and a pair of supporting plates 138. The radiation source 130 can be rotated in direction A and direction B in FIG. 2 around the supporting shaft 136, and can be rotated together with the supporting plates 138 in direction C and direction D in FIG. 2 around a tangent line of the arc of the C arm 140.

A C arm holding portion 144, that holds the C arm 140 such that the C arm 140 can rotate clockwise and counterclockwise in FIG. 2, is provided at a position that abuts the outer periphery of the cylindrical surface of the C arm 140. The C arm holding portion 144 is held, via a C arm holding portion 146, at a support 148 so as to freely move vertically. Further, the C arm holding portion 144 is supported so as to be able to rotate around a horizontal axis with respect to the C arm holding portion 146.

The radiation generator 34 has a main body 150 that incorporates therein a communication interface 132, a radiation source controller 134, and the like that are described below. The lower end of the support 148 is mounted to a support supporting section 152 that projects-out to the side from a vicinity of the lower end portion of the housing of the main body 150.

Wheels 154 are provided at the bottom portion of the main body 150, such that the radiation generator 34 can move within the hospital.

The cradle 40 and the console 42 are set in a vicinity of a wall in the radiographic image capturing room 44 relating to the present exemplary embodiment.

A housing portion 40A that can house the electronic cassette 32 is formed in the cradle 40.

When the electronic cassette 32 stands by, the electronic cassette 32 is housed in the housing portion 40A of the cradle 40 and the built-in battery is charged, and when a radiographic image is to be captured, the electronic cassette 32 is removed from the cradle 40 and disposed in the area of the patient 30 of which an image is to be captured, or mounted on the attachment structure 142 of the C arm 140 of the radiation generator 34.

The electronic cassette 32 is not limited to being used in the operating room 44 and can also be applied to medical screenings and rounds inside a hospital, for example.

Figure 3:
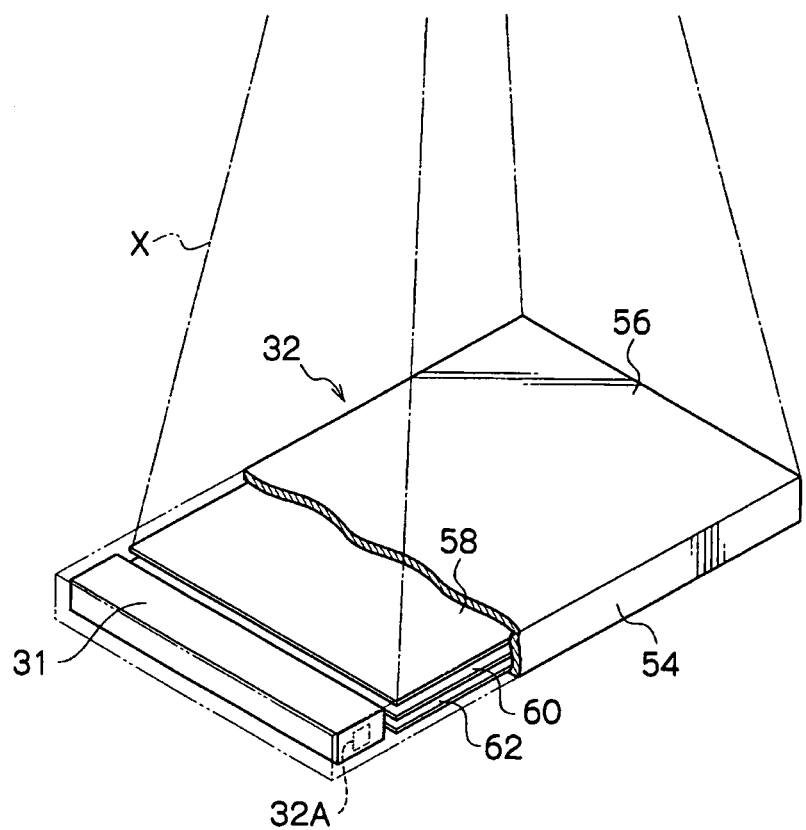
FIG. 3 is a transparent perspective view showing the internal structure of an electronic cassette relating to the exemplary embodiment.

FIG. 3 shows the internal configuration of the electronic cassette 32 pertaining to the exemplary embodiment.

As shown in FIG. 3, the electronic cassette 32 is equipped with a casing 54 formed by a material that allows the radiation X to be transmitted therethrough, and the electronic cassette 32 is configured to have a waterproof and hermetic structure. There is the fear that blood or other contaminant may adhere to the electronic cassette 32 when the electronic cassette 32 is used in an operating room or the like. Thus, the electronic cassette 32 is configured to have a waterproof and hermetic structure and is washed with an antiseptic as needed, so that the one electronic cassette 32 can be used repeatedly.

Inside the casing 54, there are disposed, in order from an irradiated surface 56 of the casing 54 that is irradiated with the radiation X, a grid 58 that removes scattered radiation of the radiation X resulting from the patient, the radiation detector 60 that detects the radiation X that has been transmitted through the patient, and a lead plate 62 that absorbs back scattered radiation of the radiation X. The irradiated surface 56 of the casing 54 may also be configured by the grid 58. A connection terminal 32A for connecting a cable 43 is provided at a side of the casing 54.

A case 31 that houses electronic circuits including a microcomputer and a rechargeable secondary battery is disposed on one end side of the inside of the casing 54. The radiation detector 60 and associated electronic circuits are actuated by power supplied from the secondary battery disposed in the case 31. A lead plate or the like may be disposed on the irradiated surface 56 side of the case 31 in order to avoid a situation where the various circuits housed inside the case 31 sustain damage in accompaniment with being irradiated with the radiation X. In the present exemplary embodiment, the electronic cassette 32 is configured as a rectangular parallelepiped shape in which the irradiated surface 56 is formed in a rectangle shape, and the case 31 is disposed at one side in a longitudinal direction of the rectangular parallelepiped shape.

Next, main portions of the electrical system of the capturing system 18 relating to the exemplary embodiment will be described in reference with FIG. 4.

A connection terminal 34A for performing communication with the console 42 is provided in the radiation generator 34. A connection terminal 42A for performing communication with the radiation generator 34, a connection terminal 42B for performing communication with the electronic cassette 32 are provided in the console 42. The connection terminal 34A of the radiation generator 34 and the connection terminal 42A of the console 42 are connected with a cable 35.

When the electronic cassette 32 performs wired communication, the cable 43 is connected to the connection terminal 32A and the electronic cassette 32 is connected to the console 42 via the cable 43.

The radiation detector 60 built into the electronic cassette 32 may employ either indirect conversion method in which radiation is first converted into light with a scintillator, and then converted to electric charges with a photoelectric conversion element such as photodiode, or direct conversion method in which radiation is directly converted into charges with a semiconductor layer such as amorphous selenium layer. The radiation detector 60 of direct conversion method is configured by a photoelectric conversion layer that absorbs and converts the radiation X into electric charges being layered on a TFT active matrix substrate 66. The photoelectric conversion layer contains, for example, amorphous selenium (a-Se) whose main component (e.g., having a content percentage equal to or greater than 50%) is selenium, and when the photoelectric conversion layer is irradiated with the radiation X, the photoelectric conversion layer converts the irradiated radiation X into electric charges by generating, inside itself, electric charges (electron-hole pairs) of an electric charge amount corresponding to the amount of the irradiated radiation X. The radiation detector 60 of indirect conversion method may, instead of a material that directly converts the radiation X into electric charges such as amorphous selenium, use a fluorescent material and a photoelectric conversion element (photodiode) to indirectly convert the radiation X into electric charges. As the phosphor material, terbium-activated gadolinium oxysulfide ($Gd_2O_2S$:Tb, called GOS) and thallium-activated cesium iodide (CsI:Tl) are known. In this case, conversion of the radiation X into light is performed by the fluorescent material, and conversion of the light into electric charges is performed by the photodiode of the photoelectric conversion element. The electronic cassette 34 of the present embodiment incorporates the radiation detector 60 of indirect conversion method.

On the TFT active matrix substrate 66, numerous pixels 74 (in FIG. 4, the photoelectric conversion layer corresponding to the individual pixels 74 and photoelectric conversion elements are schematically shown as sensor portions 72) equipped with storage capacitors 68 that store the electric charges that have been generated by the photoelectric conversion layer and TFTs 70 for reading the electric charges that have been stored in the storage capacitors 68 are arranged in a matrix. The electric charges that have been generated in the sensor portions 72 by the irradiation of the electronic cassette 32 with the radiation X are stored in the storage capacitors 68 of the individual pixels 74. Thus, the image information that had been carried in the radiation X with which the electronic cassette 32 was irradiated is converted into electric charge information (an amount of electric charge) and is held in the radiation detector 60.

Further, on the TFT active matrix substrate 66, there are disposed plural gate lines 76, which extend in one direction (row direction) and are for switching ON and OFF the TFTs 70 of the individual pixels 74, and plural data lines 78, which extend in a direction (column direction) orthogonal to the gate lines 76 and are for reading the stored electric charges from the storage capacitors 68 via the TFTs 70 that have been switched ON. The individual gate lines 76 are connected to a gate line driver 80, and the individual data lines 78 are connected to a signal processor 82. When the electric charges are stored in the storage capacitors 68 of the individual pixels 74, the TFTs 70 of the individual pixels 74 are switched ON in order in row units by signals that are supplied via the gate lines 76 from the gate line driver 80. The electric charges that are stored in the storage capacitors 68 of the pixels 74 whose TFTs 70 have been switched ON are transmitted through the data lines 78 as electric charge signals and are inputted to the signal processor 82. Consequently, the electric charges that are stored in the storage capacitors 68 of the individual pixels 74 are read in order in row units.

The gate line driver 80 according to the exemplary embodiment is capable of switching image reading modes (methods) between: a sequential-scanning method (called a progressive scanning method) in which, during one time of a image reading operation, ON signals are output in sequence from the gate line driver 80 to all of the gate lines 76 and the electrical charges that have been accumulated in all of the pixels 74 are read; and a skip-scanning method (called an interlace scanning method) in which the gate lines 76 are divided by row into odd numbered rows and even numbered rows, and, for each image reading operation, ON signals are output in sequence alternately to either the gate lines 76 in the odd numbered rows or the even numbered rows, and the electrical charges that have been accumulated in each of the pixels 74 are read one line at a time.

Figure 5:
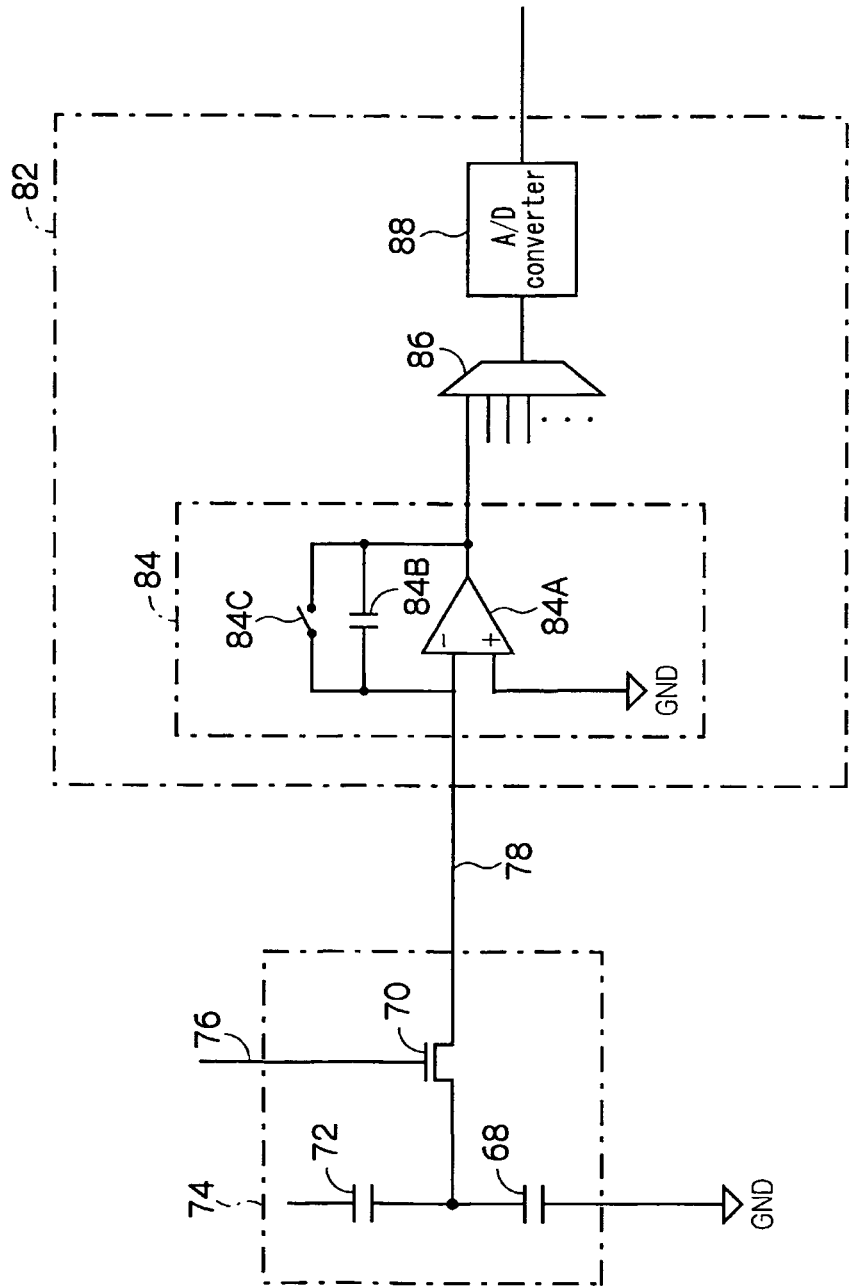
FIG. 5 is an equivalent circuit diagram that focuses on one pixel of a radiation detector relating to the exemplary embodiment.

FIG. 5 shows an equivalent circuit diagram focusing on one pixel of the radiation detector 60 pertaining to the exemplary embodiment.

As shown in FIG. 5, a source of the TFT 70 is connected to the data line 78, and the data line 78 is connected to the signal processor 82. Further, a drain of the TFT 70 is connected to the storage capacitor 68 and to the sensor portion 72, and a gate of the TFT 70 is connected to the gate line 76.

The signal processor 82 is equipped with a sample/hold circuit 84 for each of the individual data lines 78. The electric charge signals that have been transmitted through the individual data lines 78 are held in the sample/hold circuits 84. The sample/hold circuit 84 includes an operational amplifier (op-amp) 84A and a capacitor 84B and converts the electric charge signal into an analog voltage. Further, a switch 84C is disposed in the sample/hold circuit 84. The switch 84C serves as a reset circuit that causes both electrodes of the capacitor 84B to short to cause the electric charge stored in the capacitor 84B to be discharged as a result of the switch 84C being switched ON.

A multiplexer 86 and an analog/digital (A/D) converter 88 are connected in this order at an output side of the sample/hold circuits 84. The electric charge signals held in the individual sample/hold circuits 84 are converted into analog voltages, and the analog voltages are inputted in order (serially) to the multiplexer 86 and converted into digital image data by the A/D converter 88.

Figure 4:
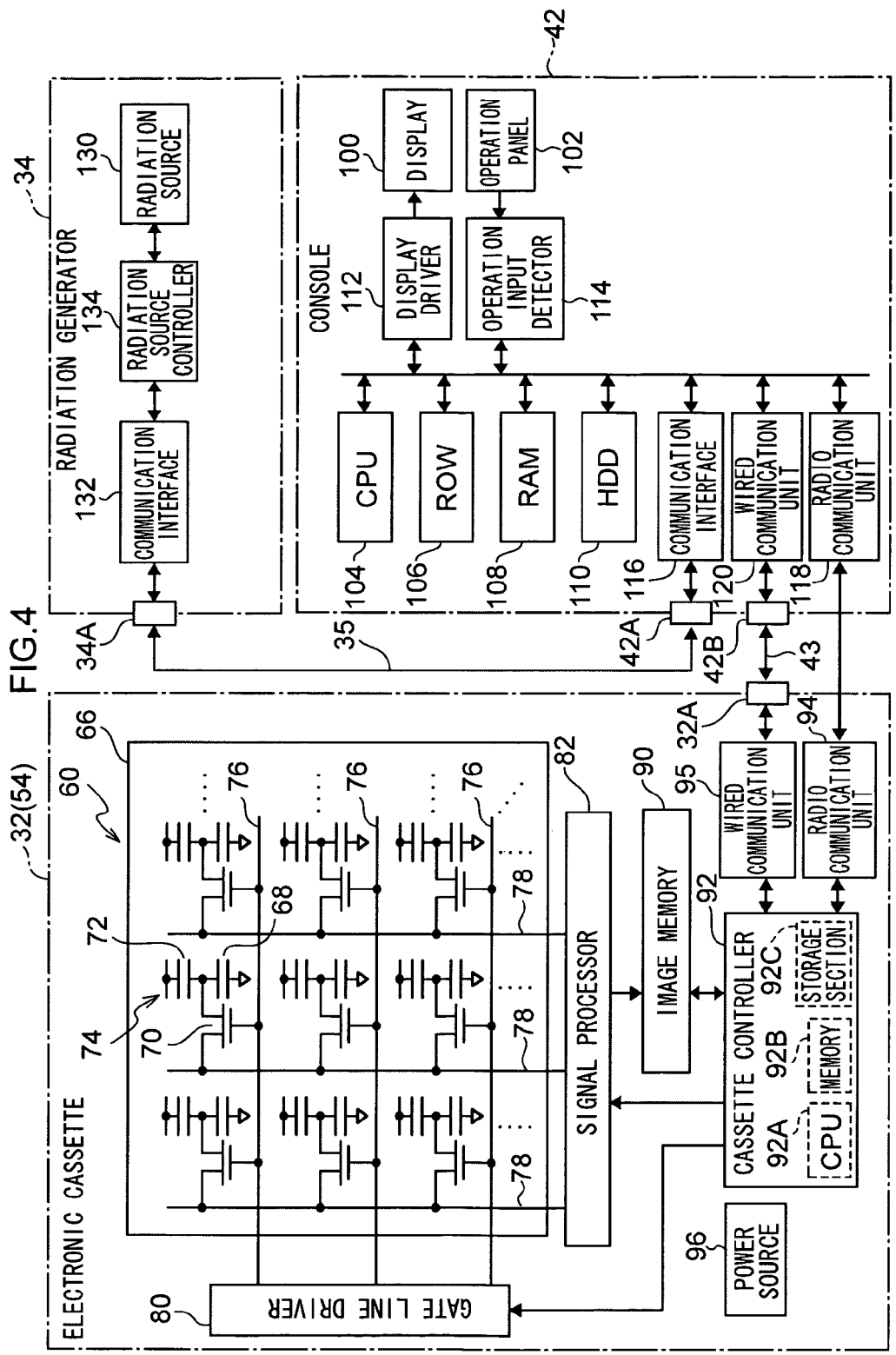
FIG. 4 is a block diagram showing the structures of main portions of the electrical system of the image capturing system relating to the exemplary embodiment.

An image memory 90 is connected to the signal processor 82 (see FIG. 4). The image data that have been outputted from the A/D converter 88 of the signal processor 82 are stored in order in the image memory 90. The image memory 90 has a storage capacity that is capable of storing plural frames' worth of image data representing a radiographic image, and each time capturing of a radiographic image is performed, image data obtained by the capturing is sequentially stored in the image memory 90.

The image memory 90 is connected to the cassette controller 92 that controls operation of the entire electronic cassette 32. The cassette controller 92 is realized by a microcomputer, and includes a central processing unit (CPU) 92A, a memory 92B including a read only memory (ROM) and a random access memory (RAM), and an non-volatile storage section 92C that may formed of a hard disk drive (HDD), flash memory or the like.

The cassette controller 92 is connected to the gate line driver 80 and controls the read-out mode of an image of the gate line driver 80. A radio communication unit 94 and a wired communication unit 95 are connected to the cassette controller 92. The radio communication unit 94 is adapted to a wireless local area network (LAN) specification represented by for example Institute of Electrical and Electronics Engineers (IEEE) 802.11a/b/g/n and controls the transmission of various types of information between the electronic cassette 32 and an external device by radio communication. The wired communication unit 95 is connected to the connection terminal 32A and controls the transmission of various types of information between the electronic cassette 32 and the console 42 via the connection terminal 32A and the cable 43. The cassette controller 92 can perform communication with the console 42 via the radio communication unit 94 or the wired communication unit 95, and transmits various types of information to and receives various types of information from the console 42 via the radio communication unit 94 or the wired communication unit 95. The cassette controller 92 stores exposure conditions received via the radio communication unit 94 or the wired communication unit 95 and read-out mode information (data), which will be described later, and starts reading out of charges based on the exposure conditions.

A power source 96 is provided in the electronic cassette 32, and the various circuits and elements mentioned above (such as microcomputers that functions as the gate line driver 80, the signal processor 82, the image memory 90, the radio communication unit 94, the wired communication unit 95, and the cassette controller 92) are actuated by power supplied from the power source 96. The power source 96 has a built-in battery (a rechargeable secondary battery) so as to not impair the portability of the electronic cassette 32, and the power source 96 supplies power to the various circuits and elements from the charged battery. In FIG. 4, wirings connecting the various circuits and elements and the power source 96 are omitted.

The console 42 is configured as a server computer and is equipped with a display 100, which displays operation menus and radiographic images that have been captured, and an operation panel 102, which includes plural keys and by which various types of information and operation instructions are inputted.

Further, the console 42 pertaining to the exemplary embodiment is equipped with a central processing unit (CPU) 104 that controls operation of the entire device, a read-only memory (ROM) 106 in which various programs including a control program are stored beforehand, a random-access memory (RAM) 108 that temporarily stores various types of data, a hard disk drive (HDD) 110 that stores and maintains various types of data, a display driver 112 that controls the display of various types of information on the display 100, and an operation input detector 114 that detects states of operation with respect to the operation panel 102. The console 42 further includes a communication interface 116 that is connected to the connection terminal 42A and transmits various types of information to and receives various types of information from the radiation generator 34 via the connection terminal 42A and the cable 35 such as the exposure conditions which will be described later, a radio communication unit 118 that transmits various types of information to and receives various types of information from the radiation generator 34 such as the exposure conditions and the read-put mode data, and a wired communication unit 120 that is connected to the connection terminal 42B and transmits various types of information to and receives various types of information from the electronic cassette 32 such as image data and the read-put mode data via the connection terminal 42B and the cable 43.

The CPU 104, the ROM 106, the RAM 108, the HDD 110, the display driver 112, the operation input detector 114, the communication interface 116, the radio communication unit 118, and the wired communication unit 120 are interconnected via a system bus BUS. Consequently, the CPU 104 can access the ROM 106, the RAM 108 and the HDD 110, can control the display of various types of information on the display 100 via the display driver 112, can control the transmission of various types of information to and the reception of various types of information from the radiation generator 34 via the communication interface 116, can control the transmission of various types of information to and the reception of various types of information from the electronic cassette 32 via the radio communication unit 118, and can control the transmission of various types of information to and the reception of various types of information from the electronic cassette 32 via the wired communication unit 120. Further, the CPU 104 can grasp states of operation by a user with respect to the operation panel 102 via the operation input detector 114.

The radiation generator 34 is equipped with the radiation source 130 that outputs the radiation X, a communication interface 132 that transmits various types of information to and receives various types of information from the console 42 such as exposure conditions, and a radiation source controller 134 that controls the radiation source 130 on the basis of received exposure conditions.

The radiation source controller 134 is also realized by a microcomputer, stores the received exposure conditions, and causes the radiation source 130 to irradiate the radiation X on the basis of the stored exposure conditions.

Next, the configuration of the radiation detector 60 will be described in a case in which indirect conversion method is employed that uses phosphor material and photoelectric conversion elements and converts radiation indirectly into electric charges.

Figure 6:
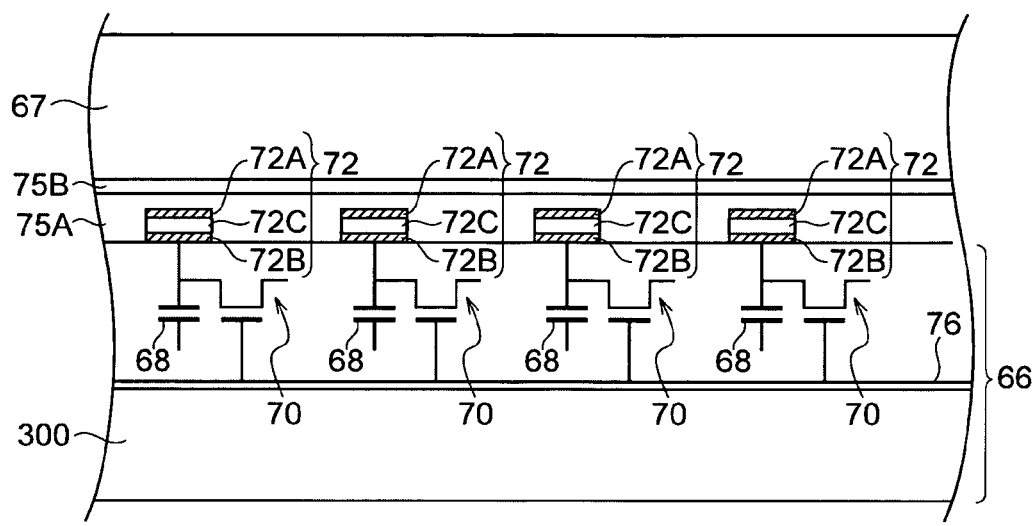
FIG. 6 is a cross-sectional view schematically showing a configuration of the radiation detector according to the exemplary embodiment.

FIG. 6 shows a schematic cross-sectional view of the configuration of the radiation detector 60 according to the present exemplary embodiment.

As shown in FIG. 6, the radiation detector 60 has a TFT active matrix substrate 66 at which thin film transistors (TFTs) 70 are formed on an insulating substrate 300.

A scintillator 67 that converts incident radiation into light is formed on the TFT active matrix substrate 66. For example, CsI:Tl or GOS ($Gd_2O_2S$:Tb) can be used as the scintillator 67. Note that the scintillator 67 is not limited to these materials.

Preferably the wavelength region of light emitted by the scintillator 67 is in the visible light region (wavelengths from 360 nm to 830 nm), and more preferably includes a green wavelength region to enable monochrome image capture with the radiation detector 60.

Specifically, fluorescent materials employed in the scintillator 67 preferably include cesium iodide (CsI) for cases in which X-rays are employed as radiation, and particularly preferably include thallium doped cesium iodide (CsI (Tl)) having an emission spectrum of wavelengths 420 nm to 700 nm during X-ray irradiation. The emission peak wavelength of CsI (Tl) in the visible light region is at 565 nm.

Vapor deposition onto a vapor deposition substrate may be employed to form the scintillator 67 by, for example, by columnar crystals of CsI (Tl) or the like. Often an Al plate is employed for the vapor deposition substrate in cases in which the scintillator 67 is formed thus by vapor deposition, due to its X-ray transmissivity and cost perspective, however there is no limitation thereto. For cases in which GOS is employed as the scintillator 67, the scintillator 67 may be formed by coating GOS on the front face of the TFT active matrix substrate 66 without using a vapor deposition substrate.

Any substrate having light transmissivity and low absorption to radiation may be employed for the insulating substrate 300 and, for example, a glass substrate, a transparent ceramic substrate, or a light transmitting resin substrate can be employed. The insulating substrate 300 is not limited to these materials.

Photoelectric conversion layers 72C, that generate charges due to the light converted by the scintillator 67 being incident thereon, are disposed between the scintillator 67 and the TFT active matrix substrate 66. Bias electrodes 72A for applying bias voltage to the photoelectric conversion layers 72C are formed on the scintillator 67 side surfaces of the photoelectric conversion layers 72C.

Charge collecting electrodes 72B, that collect the charges generated at the photoelectric conversion layers 72C, are formed at the TFT active matrix substrate 66. At the TFT active matrix substrate 66, the charges collected at the respective charge collecting electrodes 72B are read-out by the TFTs 70.

A flattening layer 75A for planarizing the TFT active matrix substrate 66 is formed on the TFT active matrix substrate 66. A bonding layer 75B for bonding the scintillator 67 to the TFT active matrix substrate 66 is formed on the flattening layer 75A and between the scintillator 67 and the TFT active matrix substrate 66.

The photoelectric conversion layers 72C absorb light that has been generated from the scintillator 67, and generates charge according to the light that has been absorbed. The photoelectric conversion layers 30 may be formed from a material that generates charge on illumination with light, and can, for example, be formed from amorphous silicon, an organic photoelectric conversion material, or the like. Photoelectric conversion layers 72C containing amorphous silicon have a wide absorption spectrum and can absorb light that has been generated in the scintillator 67. Photoelectric conversion layers 72C containing an organic photoelectric conversion material have an absorption spectrum with a sharp peak in the visible light region, and there is substantially no absorption by the photoelectric conversion layers 72C of electromagnetic waves other than the light generated by the scintillator 67, thereby enabling effective suppression of noise generation by absorption of radiation, such as X-rays or the like, in the photoelectric conversion layers 72C.

In order to most efficiently absorb the light that is emitted at the scintillator 67, it is preferable that the absorption peak wavelength of the organic photoelectric conversion material that structures the photoelectric conversion layer 72C be nearer to the emission peak wavelength of the scintillator 67. It is ideal that the absorption peak wavelength of the organic photoelectric conversion material and the emission peak wavelength of the scintillator 67 coincide, but if the difference therebetween is small, the light emitted from the scintillator 67 can be absorbed sufficiently. Specifically, it is preferable that the difference between the absorption peak wavelength of the organic photoelectric conversion material and the emission peak wavelength, with respect to radiation, of the scintillator 67 be within 10 nm, and it is more preferable for the difference to be within 5 nm.

Examples of organic photoelectric conversion materials that can satisfy such a condition are, for example, quinacridone organic compounds and phthalocyanine organic compounds. For example, the absorption peak wavelength in the visible range of quinacridone is 560 nm. Therefore, if quinacridone is used as the organic photoelectric conversion material and CsI(Tl) is used as the material of the scintillator 67, the difference in the peak wavelengths can be made to be within 5 nm, and the amount of charges generated at the photoelectric conversion layer 72C can be made to be substantially the maximum.

Specific explanation now follows of regarding the photoelectric conversion layers 72C applicable to the radiation detector 60 according to the present exemplary embodiment.

Electromagnetic wave absorption/photoelectric conversion region at the radiation detector 60 can be structured by the charge collecting electrode 72B and the bias electrode 72A that form a pair, and an organic layer that contains the organic photoelectric conversion layer 72C that is sandwiched between the charge collecting electrode 72B and the bias electrode 72A. This organic layer can be formed by the stacking of or the combining of a region that absorbs electromagnetic waves, a photoelectric conversion region, an electron transport region, a hole transport region, an electron blocking region, a hole blocking region, a crystallization preventing region, electrodes, an interlayer contact improving region, and the like.

It is preferable that the organic layer contain an organic p-type compound or an organic n-type compounds.

An organic p-type semiconductor (compound) is a donor organic semiconductor (compound) exemplified mainly by hole-transporting organic compounds, and means an organic compound that has the property that it easily donates electrons. More specifically, an organic p-type semiconductor (compound) means, when two organic materials are used by being made to contact one another, the organic compound whose ionization potential is smaller. Accordingly, any organic compound can be used as the donor organic compound, provided that it is an electron-donating organic compound.

An organic n-type semiconductor (compound) is an accepter organic semiconductor (compound) exemplified mainly by electron-transporting organic compounds, and means an organic compound that has the property that it easily accepts electrons. More specifically, an organic n-type semiconductor (compound) means, when two organic compounds are used by being made to contact one another, the organic compound whose electron affinity is greater. Accordingly, any organic compound can be used as the accepter organic compound, provided that it is an electron-accepting organic compound.

Materials that can be used as the organic p-type semiconductor and the organic n-type semiconductor, and the structure of the photoelectric conversion layer 72C, are described in detail in JP-A No. 2009-32854, which is incorporated by reference herein, and therefore, description thereof is omitted. Note that the photoelectric conversion layers 72C may be formed so as to further include fullerenes and/or carbon nanotubes.

It suffices for the sensor portion 72 that structures each pixel 74 of the radiation detector 60 to include at least the charge collecting electrode 72B, the photoelectric conversion layer 72C and the bias electrode 72A. However, in order to suppress an increase in dark current, it is preferable that the sensor portion 72 be provided with at least one of an electron blocking film and a hole blocking film, and it is more preferable that the sensor portion 72 be provided with the both.

The electron blocking film can be provided between the charge collecting electrode 72B and the photoelectric conversion layer 72C. The electron blocking film can suppress the injection of electrons from the charge collecting electrode 72B into the photoelectric conversion layer 72C and an increase in dark current, when bias voltage is applied between the charge collecting electrode 72B and the bias electrode 72A.

An electron-donating organic material can be used for the electron blocking film.

It suffices to select the material, that is actually used for the electron blocking film, in accordance with the material of the electrode adjacent thereto, the material of the photoelectric conversion layer 72C adjacent thereto, and the like. It is preferable that the material have an electron affinity (Ea) that is 1.3 eV or more greater than the work function (Wf) of the material of the electrode adjacent thereto, and have an ionization potential (Ip) that is equal to or smaller than the ionization potential of the material of the photoelectric conversion layer 72C adjacent thereto. Materials that can be used as this electron-donating organic material are described in detail in JP-A No. 2009-32854, and therefore, description thereof is omitted.

In order to reliably exhibit a dark current suppressing effect and to prevent a decrease in the photoelectric conversion efficiency of the sensor portion 72, it is preferable that the thickness of the electron blocking film be from 10 nm to 200 nm, and more preferable that the thickness be from 30 nm to 150 nm, and particularly preferable that the thickness be from 50 nm to 100 nm.

The hole blocking film can be provided between the photoelectric conversion layer 72C and the bias electrode 72A. The hole blocking film can suppress the injecting of holes from the bias electrode 72A into the photoelectric conversion layer 72C and an increase in dark current, when bias voltage is applied between the charge collecting electrode 72B and the bias electrode 72A.

An electron-accepting organic material can be used for the hole blocking film.

In order to reliably exhibit a dark current suppressing effect and to prevent a decrease in the photoelectric conversion efficiency of the sensor portion 72, it is preferable that the thickness of hole blocking film be from 10 nm to 200 nm, and more preferable that the thickness be from 30 nm to 150 nm, and particularly preferable that the thickness be from 50 nm to 100 nm.

It suffices to select the material, that is actually used for the hole blocking film, in accordance with the material of the electrode adjacent thereto, the material of the photoelectric conversion layer 72C adjacent thereto, and the like. It is preferable that the material have an ionization potential (Ip) that is 1.3 eV or more greater than the work function (Wf) of the material of the electrode adjacent thereto, and have an electron affinity (Ea) that is equal to or greater than the electron affinity of the material of the photoelectric conversion layer 72C adjacent thereto. Materials that can be used as this electron-accepting organic material are described in detail in JP-A No. 2009-32854, and therefore, description thereof is omitted.

Note that the position of the electron blocking film and the hole blocking film may be reversed in cases in which there is a bias voltage set such that holes from charges generated in the photoelectric conversion layer 72C move towards the bias electrode 72A, and electrons from the charges move towards the charge collecting electrode 72B. In is not necessary to provide both the electron blocking film and the hole blocking film; a certain degree of dark current suppressing effect can be obtained as long as one or other thereof is provided.

Figure 7:
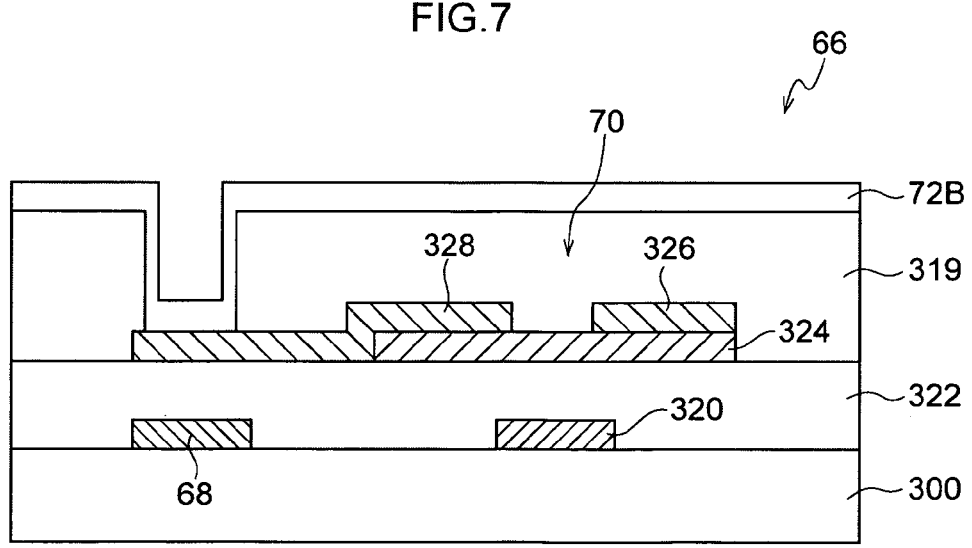
FIG. 7 is a cross-sectional view schematically showing a configuration of a TFT active matrix substrate according to the exemplary embodiment.

The structure of the TFT 70 is shown schematically in FIG. 7.

In the TFT active matrix substrate 66, storage capacitors 68 and the TFTs 70 are formed corresponding to the charge collecting electrodes 72B. The storage capacitors 68 store charges moved toward the charge collecting electrodes 72B. TFTs 70 converts the charges stored in the storage capacitors 68 into electric signal and outputs the electric signal. The region in which each of the TFTs 70 is formed has a portion that overlaps with the charge collecting electrode 72B in plan view. By configuring thus, the TFTs 70 and the sensor portions 72 overlap along the thickness direction in each of the pixels. Note that in order to minimized the surface area of the radiation detector 60 (pixels) the regions formed with the storage capacitors 68 and the TFTs 70 are preferably completely covered by the charge collecting electrodes 72B.

The storage capacitors 68 are electrically connected to the corresponding charge collecting electrodes 72B via wirings formed by conductive materials and penetrating an insulating film 319 that is disposed between the insulating substrate 300 and the charge collecting electrodes 72B. Thereby, charges collected at the charge collecting electrodes 72B can be moved to the storage capacitors 68.

At the TFT 70, a gate electrode 320, a gate insulating film 322 and an active layer (channel layer) 324 are layered, and further, the TFT 70 is structured such that a source electrode 326 and a drain electrode 328 are formed on the active layer 324 with a predetermined interval therebetween.

The active layer 324 can, for example, be formed from amorphous silicon, a amorphous (non-crystalline) oxide, an organic semiconductor material, carbon nanotubes or the like. Note that the material for forming the active layer 324 is not limited to these materials.

As the amorphous oxide that can structure the active layer 324, oxides containing at least one of In, Ga and Zn (e.g., In—O types) are preferable, oxides containing at least two of In, Ga and Zn (e.g., In—Zn—O types, In—Ga—O types, Ga—Zn—O types) are more preferable, and oxides containing In, Ga and Zn are particularly preferable. As an In—Ga—Zn—O type amorphous oxide, amorphous oxides whose composition in a crystal state is expressed by $InGaO_3(ZnO)_m$ (where m is a natural number of less than 6) are preferable, and in particular, $InGaZnO_4$ is more preferable. Note that amorphous oxide that can form the active layer 324 is not limited to these.

Possible organic semiconductor materials for configuring the active layer 324 include phthalocyanine compounds, pentacene, vanadyl phthalocyanine and the like, however there is no limitation thereto. Since explanation of details regarding structures of such phthalocyanine compounds is given in JP-A No. 2009-212389, which is incorporated by reference herein, further explanation is omitted.

By forming the active layer 324 of the TFTs 70 from amorphous oxides, organic semiconductor materials, or carbon nanotubes, since there is no absorption of radiation such as X-rays, or any absorption is restricted to an extremely small amount, noise generation in the TFTs 70 can be effectively suppressed.

When the active layer 324 is formed with carbon nanotubes, the switching speed of the TFTs 70 can be increased, and the TFTs 70 can be formed having a low degree of absorption of light in the visible light region. Note that in cases in which the active layer 324 is formed with carbon nanotubes, since the performance of the TFTs 70 deteriorates significantly with incorporation of only a minute amount of metal impurity in the active layer 324, extremely high purity carbon nanotubes need to be separated or extracted, such as by centrifugal separation, for formation.

In order to implement the skip-scanning method, it is preferable to adopt a material that can realize low gate driving voltage for the TFT 70. In the TFT 70, the following amount (Q) of charge feed-through is generated when the TFT 70 is driven ON or OFF:

$$Q = C_{stray} \times \Delta V,$$

where $C_{stray}$ is a stray capacitance of the gate electrode, and $\Delta V$ is a voltage difference between ON voltage and OFF voltage in the gate driving voltage.

In the TFT active matrix substrate 66, when an image is read-out using the skip-scanning method, charge feed-through generated in a line which is being read-out would partially cause noise in the adjacent line, which is skipped and not yet read, due to charge injection in the adjacent line. As a result, a value of unstable charge due to the charge feed-through may be superimposed on that of the original charge to be read when the charge of the skipped line is read. In fluoroscopic imaging in which the amount of charge generated is relatively small, this would have significant impact on the resultant image since the level of feed-though charge is at or above the level of charge generated by radiation, such that it appears as noise in line form parallel to the gate lines and the resultant image may be deteriorated. In order to reduce this noise as much as possible, it is preferable that the difference between the gate driving voltages for driving the TFT 70 ON and OFF is as small as possible. Therefore, it is preferable for the active layer 324 to be formed using organic semiconductor materials or amorphous oxides such as In—Ga—Zn—O type amorphous oxides that can make the gate driving voltage lower than amorphous Si. Further, in terms of raising drive frequency of the TFT 70 in the interlace scanning method, using In—Ga—Zn—O type amorphous oxides having high mobility is more preferable.

The above amorphous oxides, organic semiconductor materials, carbon nanotubes and organic photoelectric conversion materials are all capable of being formed into a film at low temperature. Accordingly, the insulating substrate 300 is not limited to a substrate with high heat resistance, such as a semiconductor substrate, a quartz substrate, a glass substrate or the like, and a flexible substrate such as from a plastic, an aramid, or a bionanofiber substrate can be employed. Specifically, a flexible substrate including a polyester such as polyethylene terephthalate, polybutylene phthalate and polyethylene naphthalate, polystyrene, polycarbonate, polyethersulphone, a polyarylate, a polyimide, a polycyclic olefin, a norbornene resin, a poly (chloro trifluouro ethylene) or the like, can be employed. By employing such a plastic flexible substrate, a reduction in weight can be achieved which is beneficial to portability.

Further, an insulation layer to ensure insulation ability, a gas barrier layer for preventing moisture and oxygen transmission, an undercoat layer for flattening and/or raising adhesiveness to the electrodes, or other layers may be provided to the insulating substrate 300.

Since an aramid can be used in high temperature process applications of 200° C. or above, a transparent electrode material can be high-temperature hardened to give a low resistance, and compatibility can also be made to automatic packaging of driver ICs including solder re-flow processes. Since an aramid has a thermal expansion coefficient that is close to that of indium tin oxide (ITO) and glass substrate, post manufacture warping is small, and it is not readily broken. An aramid can also be formed in a relatively thin substrate in comparison to a glass substrate. Therefore, the insulating substrate 300 may be formed with an aramid layered on an ultrathin glass substrate.

A bionanofiber is a composite of cellulose micro-fibril bundles (bacteria cellulose), produced by the bacterium Acetobacter Xylinum, and a transparent resin. The cellulose micro-fibril bundles are, with a width of 50 nm, a size that is $1/10$ that of visible wavelengths, and have high strength, high elasticity, and low thermal expansion. By impregnating and hardening the bacteria cellulose in a transparent resin, such as an acrylic resin, an epoxy resin, a bionanofiber is obtained with a light transmissivity of 90% to light at 500 nm wavelength, while including fibers at a proportion of 60% to 70%. The bionanofiber has a low thermal expansion coefficient (3 to 7 ppm/K), comparable to that of crystalline silicon, strength comparable to steel (460 MPa), high elasticity (30 GPa) and is also flexible. This enables the insulating substrate 300 to be formed thinner in comparison to configuration with a glass substrate or the like.

In the present exemplary embodiment, the storage capacitors 68, the TFTs 70, the sensor portions 77 and a flattening layer 75A are formed in this sequence on the insulating substrate 300. The radiation detector 60 is formed by attaching the scintillator 60 above the insulating substrate 300 with a bonding layer 75B employing a bonding resin of low light absorption. The insulating substrate 300 formed up to the flattening layer 75A is referred to below as the TFT active material substrate 66.

In the present exemplary embodiment, the radiation detector 60 is incorporated in the electric cassette 32 such that radiation X is irradiated from the side having the TFT active matrix substrate 66.

Figure 8:
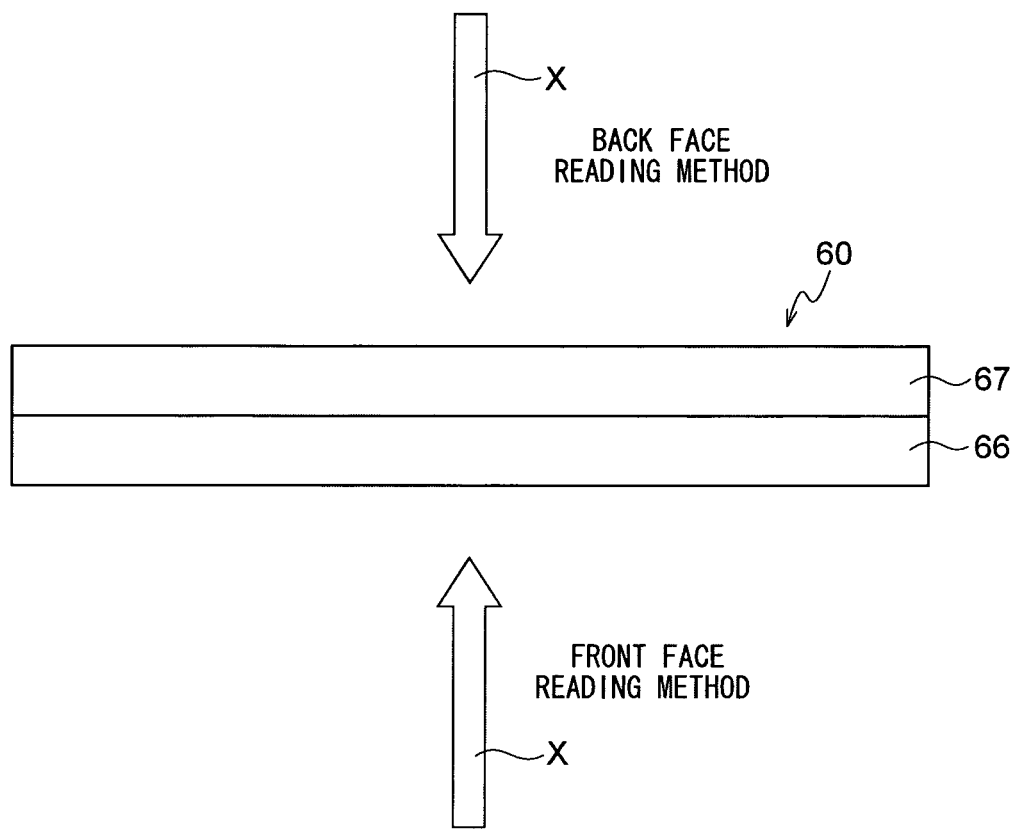
FIG. 8 is a cross-sectional side view explaining front face irradiation/back face reading method and back face irradiation/front face reading method.

As shown in FIG. 8, the radiation detector 60 may be irradiated with radiation from the side on which the scintillator 67 has been formed, and a radiographic image is read by the TFT active matrix substrate 66 which is disposed at the back side of the radiation incident surface (back face reading method, called a Penetration Side Sampling (PSS) method). In this case, there is more intense light generation at the top face side of the scintillator 67 in FIG. 8 (the opposite side to that of the TFT active matrix substrate 66). Further, the radiation detector 60 may be irradiated with radiation from the TFT active matrix substrate 66 side, and a radiographic image is read by the TFT active matrix substrate 66 disposed at the front side of the radiation incident surface (front face reading method, called an Irradiation Side Sampling (ISS) method). In this case, radiation that has passed through the TFT active matrix substrate 66 is irradiated onto the scintillator 67, and light generation is more intense at the TFT active matrix substrate 66 side of the scintillator 67. Charge is generated in each of the photoelectric conversion layers 72C provided as the TFT active matrix substrate 66 due to the light generated in the scintillator 67. Accordingly, the radiation detector 60 has a higher resolution of radiographic images obtained by image capture when image capture is performed by the front face reading method than by the back face reading method, since the light generation position in the scintillator 67 is nearer to the TFT active matrix substrate 66.

Since the photoelectric conversion layers 72C of the radiation detector 60 are formed by organic photoelectric conversion materials, the photoelectric conversion layers 72C hardly absorb any radiation. Therefore, in the radiation detector 60 of the present exemplary embodiment, even if radiation transmits through the TFT active matrix substrate 66 in the front face reading method, reduction of sensitivity with respect to the radiation X can be suppressed since a radiation absorption amount in the photoelectric conversion layers 72C is small. Since radiation reaches the scintillator 67 by transmitting through the TFT active matrix substrate 66 in the front face reading method, forming the photoelectric conversion layers 72C of the TFT active matrix substrate 66 with organic photoelectric conversion materials is suitable for the front face reading method because there is significantly little absorption of radiation and attenuation of radiation can be reduced.

Amorphous oxides that form the active layer 324 of the TFT 70 and organic photoelectric conversion materials that form the photoelectric conversion layers 72C are all capable of being formed into a film at low temperature. Therefore, the insulating substrate 300 can be formed using a plastic resin, an aramid, or a bionanofiber which absorb only a little amount of radiation. Since the thus formed insulating substrate 300 absorbs a little amount of radiation, reduction of sensitivity with respect to the radiation X can be suppressed even if radiation transmits through the TFT active matrix substrate 66 in the front face reading method.

Further, if the radiation detector 60 is attached to the irradiated surface 56 inside the casing 54 such that the TFT active matrix substrate 66 is disposed at the irradiated surface 56 side and the insulating substrate 300 is formed using rigid plastic resin, aramid, or bionanofiber, the overall radiation detector 60 becomes rigid and, therefore, the irradiated surface 56 of the casing 54 can be formed thin. Alternately, if the insulating substrate 300 is formed using flexible plastic resin, aramid, or bionanofiber, the overall radiation detector 60 will have flexibility, and the radiation detector 60 will hardly be broken even if an impact is applied to the irradiated surface 56.

Next, overall operation of the capturing system 18 pertaining to the exemplary embodiment will be described.

The electronic cassette 32 and the console 42 pertaining to the exemplary embodiment perform wired communication when they are interconnected by the communication cable 43 and perform radio communication when they are not interconnected by the communication cable 43. The capturing system 18 of the present exemplary embodiment is configured capable of selecting a capturing mode from still image capture that performs capturing one by one, or fluoroscopic imaging that performs capturing continuously. Further, capturing system 18 is configured capable of selecting continuous irradiation in which radiation is continuously irradiated from the radiation source 130 or pulse irradiation in which radiation is irradiated in pulsed form in synchronization with the frame rate of the capturing during the capturing.

When radiographic image capture is performed, one of the terminals 12 (see FIG. 1) receives an image capture request from a doctor or a radiologic technologist. In the image capture request, there are designated a patient to be captured, the area of the patient to be captured, the capturing more, and optionally the tube voltage, the tube current, the irradiation time, and the total radiation amount.

The terminal 12 notifies the RIS server 14 of the content of the received image capture request. The RIS server 14 stores, in the database 14A, the content of the image capture request which has been notified by the terminals 12.

The console 42 accesses the RIS 14 to acquire the content of the image capture request and the attribute information of a patient to be captured from the RIS server 14 and display the content of the image capture request and the attribute information of the patient on the display 100 (see FIG. 4).

An operator initiates capture of a radiographic image on the basis of the content of the image capture request displayed on the display 100.

For example, as shown in FIG. 2, when capture of a radiographic image of an affected area of the subject 48 lying on the bed 46 is to be performed, the operator disposes the electronic cassette 32 between the bed 46 and the affected area of the subject 48 in accordance with the area of image capture without connecting the cable 43 to the electronic cassette 32 and the console 42 in case of using radio communication, or after connecting the electronic cassette 32 and the console 42 with the cable 43 in case of using wired communication.

Then, at the operation panel 102, the operator designates still image capture or fluoroscopic imaging as the image capturing mode. In a case in which still image capture is designated, the operator designates, at the operation panel 102, the exposure conditions such as the tube voltage, tube current, irradiation time, and the like for the time when the radiation X is irradiated. In a case in which fluoroscopic imaging is designated, the operator designates, at the operation panel 102, the exposure conditions such as the frame rate, the tube voltage, the tube current, and the like. Further, the operator designates by which of continuous irradiation or pulse irradiation the image capturing is to be carried out.

The console 42 transmits the designated exposure conditions to the radiation generator 34 and the electronic cassette 32. The console 42 also transmits reading mode data of the progressive scanning method as the initial reading mode to the electronic cassette 32.

In response to receipt of the exposure conditions from the console 42, the radiation source controller 134 of the radiation generator 34 stores the received exposure conditions. In response to the cassette controller 92 of the electronic cassette 32 receiving the exposure conditions and the reading more data from the console 42, the cassette controller 92 stores the received exposure conditions and reading mode data in the storage section 92C.

After completion of image capture preparation, the operator performs image capture instruction operation to the operation panel 102 of the console 42.

In response to the image capture instruction operation performed to the operation panel 102, image capture operation as shown in FIG. 9 to FIG. 12 is started according to which has been designated among still image capture by continuous irradiation, still image capture by pulse irradiation, fluoroscopic imaging by continuous irradiation, or fluoroscopic imaging by pulse irradiation.

Figure 9:
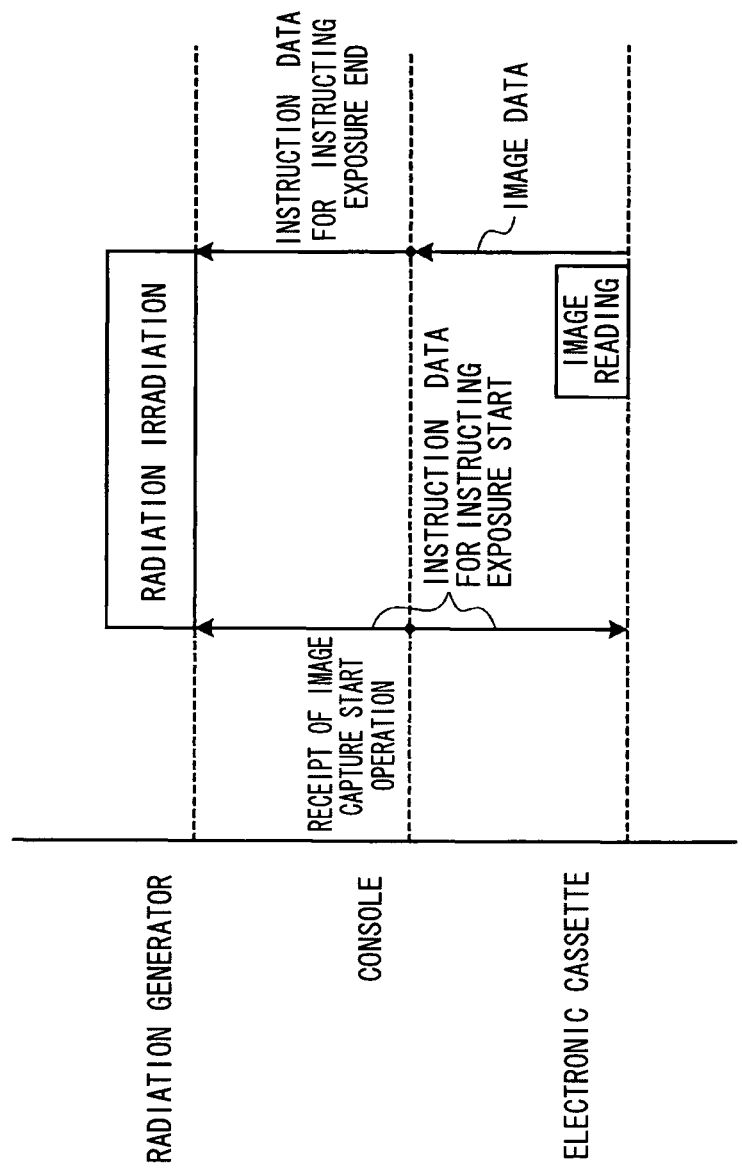
FIG. 9 is a timing chart showing a flow of image capture operation when still image capture has been designated by continuous irradiation according to the exemplary embodiment.

FIG. 9 shows a timing chart showing a flow of image capture operation when still image capture by continuous irradiation has been designated.

The console 42 transmits instruction information (data) instructing initiation of exposure to the radiation generator 34 and the electronic cassette 32 in response to image capture start operation performed on the operation panel 102.

In response to receipt of the instruction data instructing initiation of exposure, the radiation generator 34 starts generation and emission of radiation with the tube voltage and the tube current according to the exposure conditions received from the console 42.

After the irradiation period designated in the exposure conditions has elapsed since receipt of the exposure initiation instruction data, the cassette controller 92 of the electronic cassette 32 controls the gate line driver 80 such that ON signals are output from the gate line driver 80 to each of the gate lines 76 in sequence one line at a time according to the reading mode data received from the console 42. Accordingly, progressive scanning is performed in which each of the TFTs 70 connected to each of the gate lines 76 being switched ON in sequence one line at a time, thereby reading the electrical charges that have been accumulated in all of the pixels 74 in sequence one line at a time.

In the radiation detector 60, when each of the TFTs 70 connected to each of the gate lines 76 is switched ON in sequence one line at a time, electrical charges that have been accumulated in each of the storage capacitors 68 flow out as an electrical signal through each of the data lines 78 in sequence one line at a time. The electrical signals flowing out through each of the data lines 78 is converted into digital image data by the signal processor 82, stored in the image memory 90 and transmitted to the console 42.

In response to receipt of the image data, the console 42 transmits instruction data instructing end of exposure to the radiation generator 34, and also performs various image processing for correction on the received image data, such as shading correction, and stores the processed image data in the HDD 110.

The radiation generator 34 stops generating and emitting radiation in response to receipt of the instruction data instructing end of exposure.

Image data stored in the HDD 110 is displayed on the display 100, in order, for example, to check the captured radiographic image, and is also transferred to the RIS server 14 and stored in the database 14A. Accordingly, it is possible for a doctor to perform, for example, interpretation, diagnosis and the like with the captured radiographic image.

Figure 10:
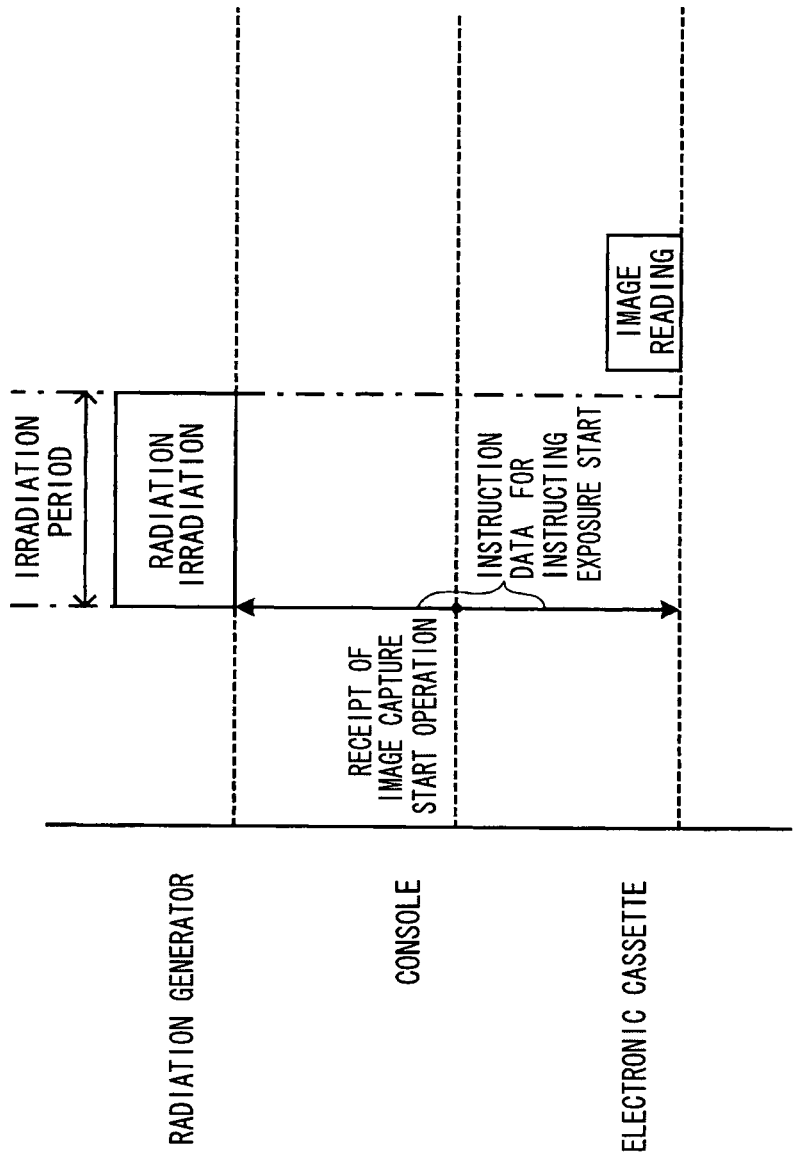
FIG. 10 is a timing chart showing a flow of image capture operation when still image capture has been designated by pulse irradiation according to the exemplary embodiment.

FIG. 10 shows a timing chart of a flow of image capture operation when still image capture by pulse irradiation has been designated.

The console 42 transmits instruction data instructing initiation of exposure to the radiation generator 34 and the electronic cassette 32 in response to image start operation being performed on the operation panel 102.

In response to receipt of the instruction data instructing initiation of exposure, the radiation generator 34 starts generation and emission of radiation with the tube voltage, tube current and irradiation duration according to the exposure conditions received from the console 42.

After the irradiation period designated in the exposure conditions has elapsed since receipt of the exposure initiation instruction data, the cassette controller 92 of the electronic cassette 32 controls the gate line driver 80 such that ON signals are output from the gate line driver 80 to the each of the gate lines 76 in sequence one line at a time according to the reading mode data received from the console 42. Accordingly, each of the TFTs 70 connected to each of the gate lines 76 are switched ON in sequence one line at a time, and progressive scanning is performed by reading the electrical charges that have been accumulated in all of the pixels 74 in sequence one line at a time. The electrical charges are thereby read from all of the pixels 74, and image data according to the electrical charges that have been accumulated in each of the pixels 74 is stored in the image memory 90. The image data stored in the image memory 90 is transmitted to the console 42, and the console 42 performs various image processing for correction on the received image data, such as shading correction, and stores the processed image data in the HDD 110. The image data stored in the HDD 110 is displayed on the display 100, in order, for example, to check the captured radiographic image, and is also transferred to the RIS server 14 and stored in the database 14A.

Figure 11:
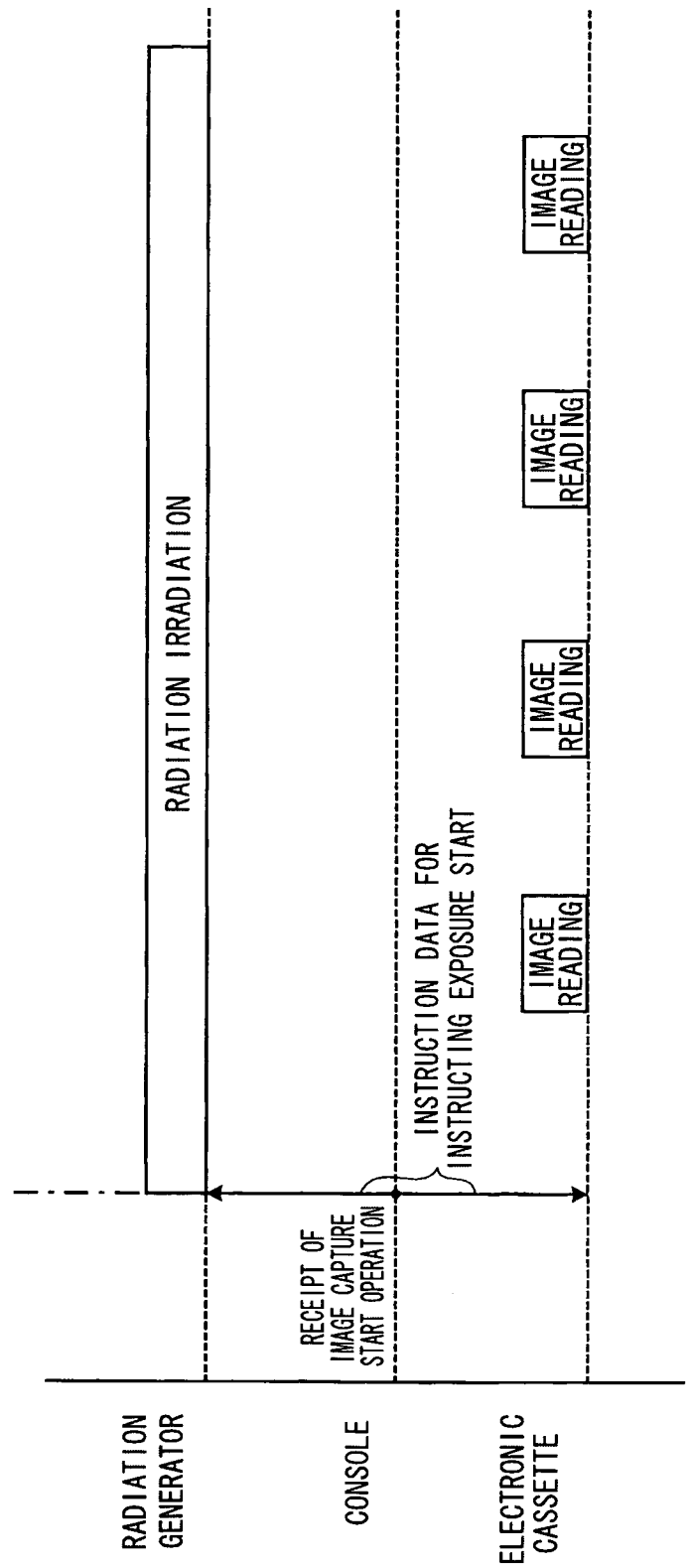
FIG. 11 is timing chart showing a flow of image capture operation when fluoroscopic imaging has been designated by continuous irradiation according to the exemplary embodiment.

FIG. 11 shows a timing chart showing a flow of image capture operation when fluoroscopic imaging by continuous irradiation has been designated.

The console 42 transmits instruction data instructing initiation of exposure to the radiation generator 34 and the electronic cassette 32 in response to image start operation being performed to the operation panel 102.

In response to receipt of the instruction data instructing initiation of exposure, the radiation generator 34 starts irradiation of radiation with the tube voltage and the tube current according to the exposure conditions received from the console 42.

In response to receipt of the instruction data instructing initiation of exposure, the cassette controller 92 of the electronic cassette 32 controls the gate line driver 80 such that ON signals are output from the gate line driver 80 to the each of the gate lines 76 in sequence one line at a time according to the reading mode data received from the console 42, and progressive scanning is repeatedly performed at the frame rate designated in the exposure conditions by switching ON each of the TFTs 70 connected to each of the gate lines 76 in sequence one line at a time, reading the electrical charges that have been accumulated in all of the pixels 74, thereby image reading at the designated frame rate. The electrical charges are thereby read from all of the pixels 74 in sequence one line at a time, and image data according to the electrical charges that have been accumulated in each of the pixels 74 is stored in the image memory 90. The image data stored in the image memory 90 is transmitted to the console 42 by one image (frame) worth of data amount at a time, and the console 42 performs various image processing for correction on the received image data, such as shading correction, and stores this image data in the HDD 110. The image data stored in the HDD 110 is displayed on the display 100, in order, for example, to check the captured radiographic image, and is also transferred to the RIS server 14 and stored in the database 14A.

In response to image capture end operation being performed to the operation panel 102, the console 42 transmits instruction data instructing end of exposure to the radiation generator 34 and the electronic cassette 32. The radiation source 130 thereby halts radiation irradiation, and image reading is ended in the electronic cassette 32.

Figure 12:
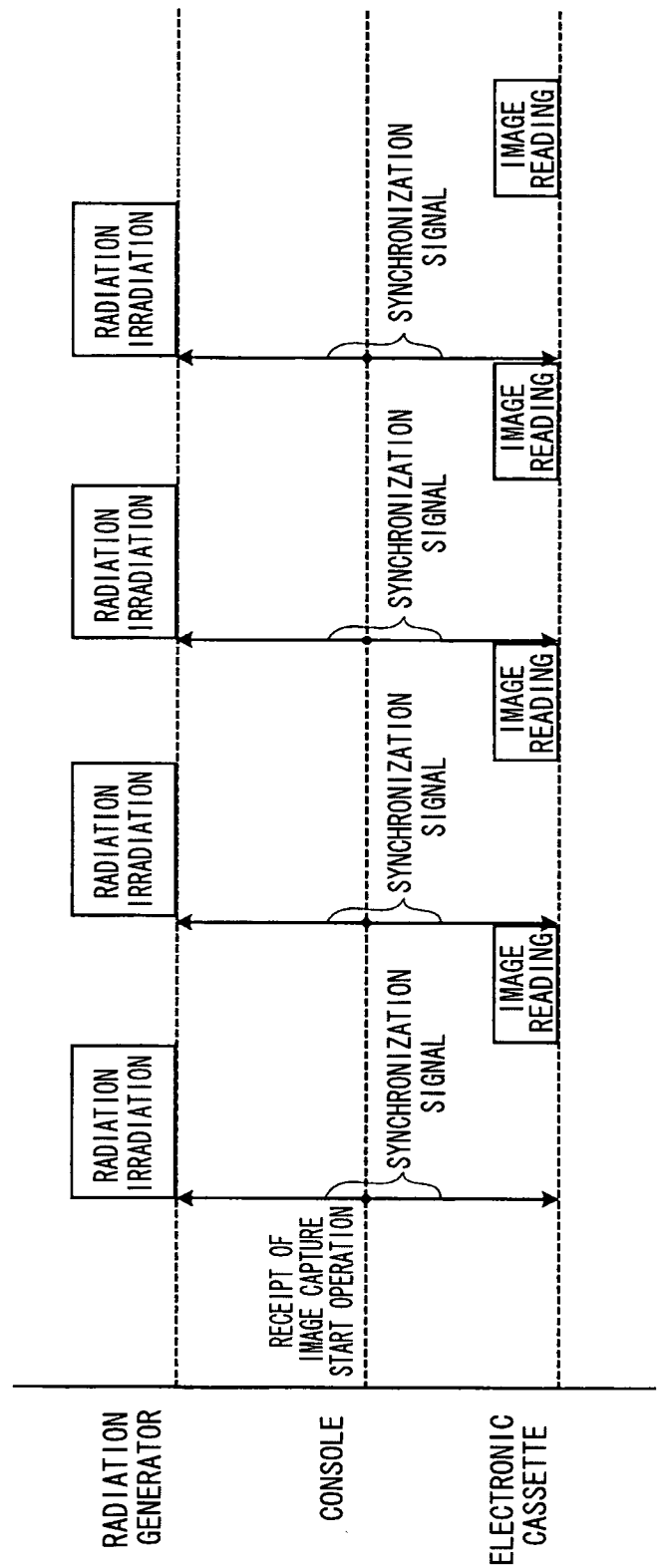
FIG. 12 is a timing chart showing a flow of image capture operation when fluoroscopic imaging has been designated by pulse irradiation according to the exemplary embodiment.

FIG. 12 shows a timing chart of a flow of image capture operation when fluoroscopic imaging by pulse irradiation has been designated.

The console 42 transmits a synchronization signal to the radiation generator 34 and the electronic cassette 32 at a cycle according to the frame rate.

The radiation generator 34 starts generation and emission of radiation with the tube voltage, the tube current and the irradiation period according to the exposure conditions received from the console 42 every time the synchronization signal is received.

After the irradiation period designated in the exposure conditions has elapsed since receipt of the synchronization signal, the cassette controller 92 of the electronic cassette 32 controls the gate line driver 80 such that ON signals are output from the gate line driver 80 to the each of the gate lines 76 in sequence one line at a time according to the reading mode data received from the console 42. Accordingly, each of the TFTs 70 connected to each of these gate lines 76 are switched ON in sequence one line at a time, and progressive scanning is performed by reading the electrical charges that have been accumulated in all of the pixels 74. The electrical charges are thereby read from all of the pixels 74 in sequence one line at a time, and image data according to the electrical charges that have been accumulated in each of the pixels 74 is stored in the image memory 90. The image data stored in the image memory 90 is transmitted to the console 42 by one image (frame) worth of data amount at a time. The console 42 performs various image processing for correction on the received image data, such as shading correction, and stores this image data in the HDD 110. The image data stored in the HDD 110 is displayed on the display 100, in order, for example, to check the captured radiographic image, and is also transferred to the RIS server 14 and stored in the database 14A.

In response to image capture end operation being performed to the operation panel 102, the console 42 transmits instruction data instructing end of exposure to the radiation generator 34 and the electronic cassette 32. The radiation source 130 thereby halts radiation irradiation, and image reading in the electronic cassette 32 is ended.

However, during fluoroscopic imaging, exposure dose to a patient increases when radiation is irradiated onto the patient for a long period of time.

In order to address this issue, the console 42 derives the cumulative radiation amount irradiated from the radiation source 130 during fluoroscopic imaging. The cumulative radiation amount can be used as a proxy for the exposure dose to a patient during fluoroscopic imaging. In order to suppress the exposure dose to a patient, the console 42 switches over (changes) the image capture mode to fluoroscopic imaging with a reduced radiation amount irradiated from the radiation source 130 when the cumulative radiation amount has exceeded a specific permitted amount.

The permitted amount may be input by the operator from the operation panel 102. Alternately, the permitted amount for irradiation of each image capture location may be pre-stored as image capture location specific permitted amount data in the HDD 110, and in response to designation of the image capture location on the operation panel 102 by the operator, a permitted amount corresponding to the designated image capture location may be obtained from the image capture location specific permitted amount data. In another embodiment, the exposure dose to a patient on a daily basis may be stored in the database 14A of the RIS server 14, and the RIS server 14 may derive the permitted exposure dose to a patient from the total value of the exposure amounts over a specific period (for example, the most recent 3 month period), and notify this permitted exposure dose as a permitted amount to the console 42.

Figure 13:
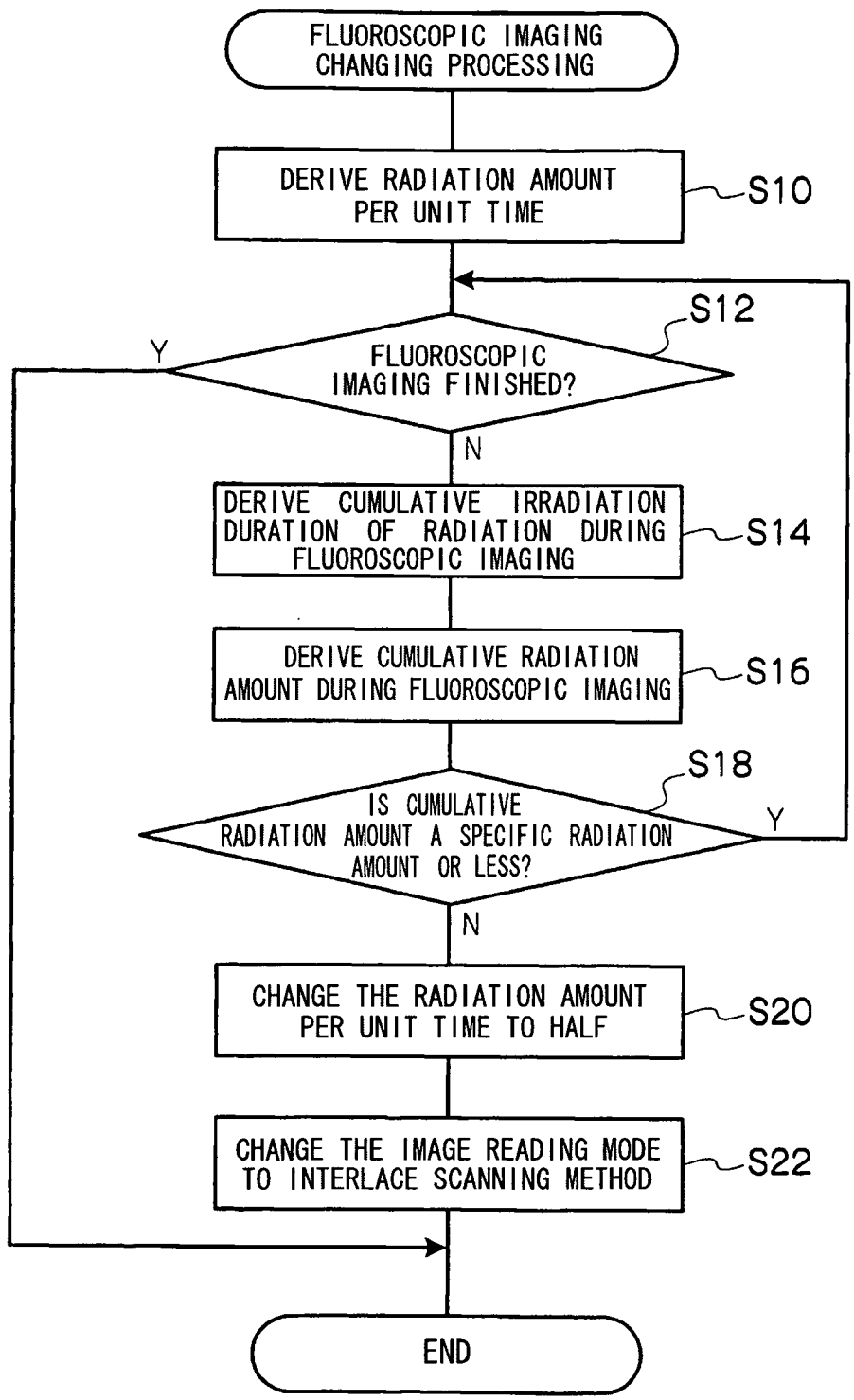
FIG. 13 is a flow chart showing a flow of a fluoroscopic imaging changing processing program according to the exemplary embodiment.

FIG. 13 shows a flow chart of processing of a fluoroscopic imaging changing processing program executed by the CPU 104 when fluoroscopic imaging is initiated. This program may be pre-stored in a specific region of the ROM 106.

At step S10 of FIG. 13, the radiation amount per unit time for irradiation from the radiation source 130 is derived based on the tube voltage and tube current designated in the instructed exposure conditions.

In the next step S12, determination is made as to whether or not fluoroscopic imaging has finished. Processing is ended in cases in which positive determination is made, and in cases in which negative determination is made processing proceeds to step S14.

At the next step S14, the cumulative irradiation duration is derived for which radiation has been irradiated from the radiation source 130 during fluoroscopic imaging. In fluoroscopic imaging by continuous irradiation, the cumulative irradiation duration is the period from the start point of fluoroscopic imaging to the current point in time. In fluoroscopic imaging by pulse irradiation, the cumulative irradiation duration is the duration arrived at by multiplying the number of times the synchronization signal was transmitted between the start point of fluoroscopic imaging and the current point in time with the irradiation period designated in the exposure conditions.

At the next step S16, the cumulative radiation amount irradiated from the radiation source 130 during fluoroscopic imaging is derived by multiplying the cumulative irradiation duration derived at step S14 with the radiation amount per unit time derived at step S10.

At step S18, determination is made as to whether or not the cumulative radiation amount derived at step S16 is the permitted amount or less. In cases in which positive determination is made processing returns again to step S12, and in cases in which negative determination is made processing proceeds to step S20.

At step S20, the tube voltage and the tube current designated in the exposure conditions are changed so as to change the radiation amount per unit time irradiated from the radiation source 130 to half thereof (for example, the tube current is changed to ½), and the changed tube voltage and tube current are transmitted to the radiation generator 34 and the electronic cassette 32.

The radiation generator 34 changes the tube voltage and/or the tube current according to the exposure conditions to the changed tube voltage and/or tube current received from the console 42 and starts radiation irradiation. The radiation amount per unit time that is irradiated from the radiation source 130 is thereby reduced to half of the previous amount.

At step S22, reading mode data designating an interlace scanning method is transmitted to the electronic cassette 32, and processing is ended.

In response to receipt of the reading mode data from the console 42, the cassette controller 92 of the electronic cassette 32 changes the image reading mode to the interlace scanning method according to the received reading mode data, and controls such that ON signals are output in sequence to the gate lines 76 of either the odd numbered rows or the even numbered rows, alternately for each image reading operation, and the electrical charges that have been accumulated in the pixels 74 are read in sequence one line at a time.

Figure 14:
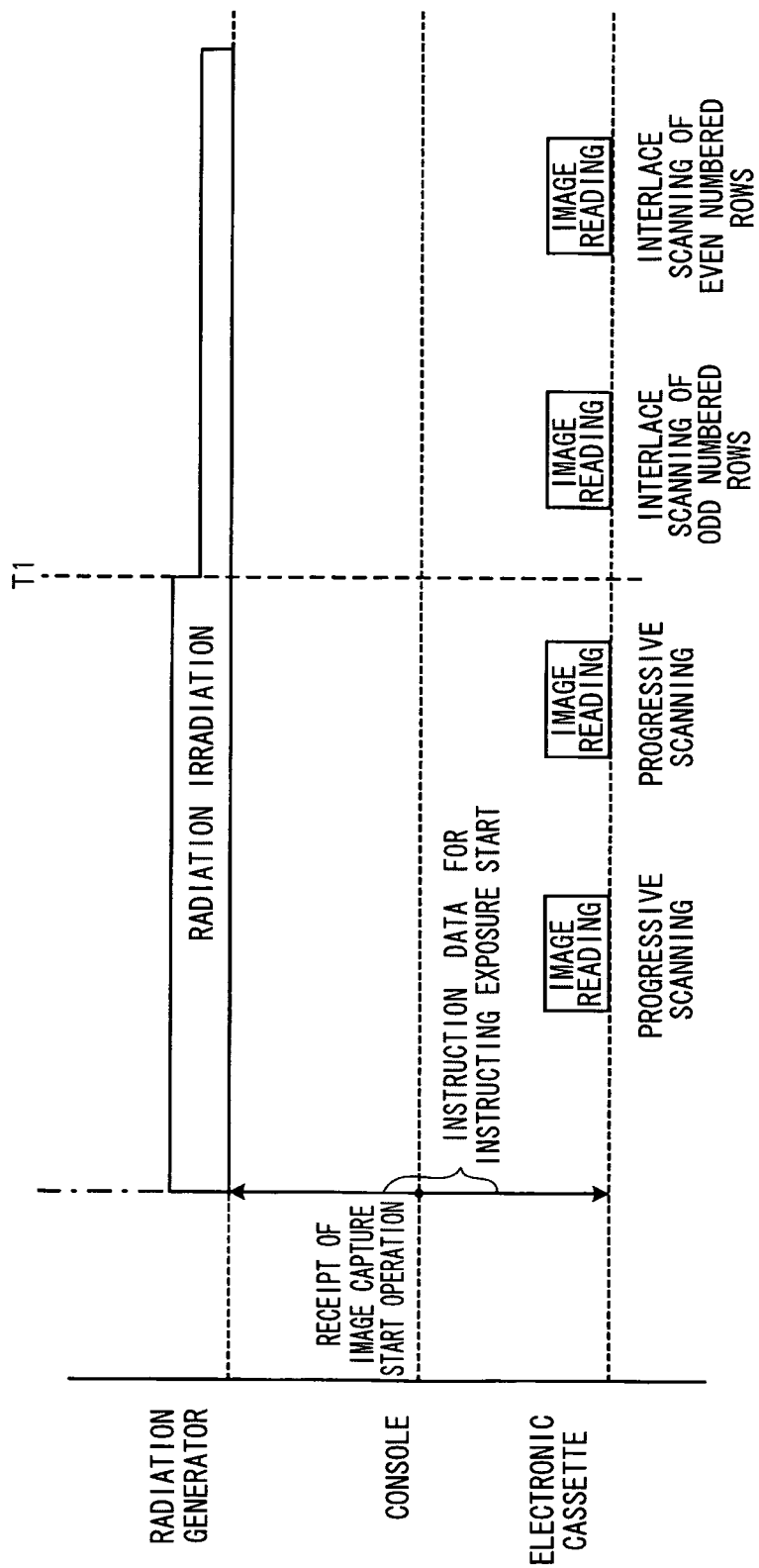
FIG. 14 is a timing chart showing a flow of image capture operation when the cumulative radiation amount irradiated from a radiation source has exceeded a permitted amount during fluoroscopic imaging by continuous irradiation according to the exemplary embodiment.
Figure 15:
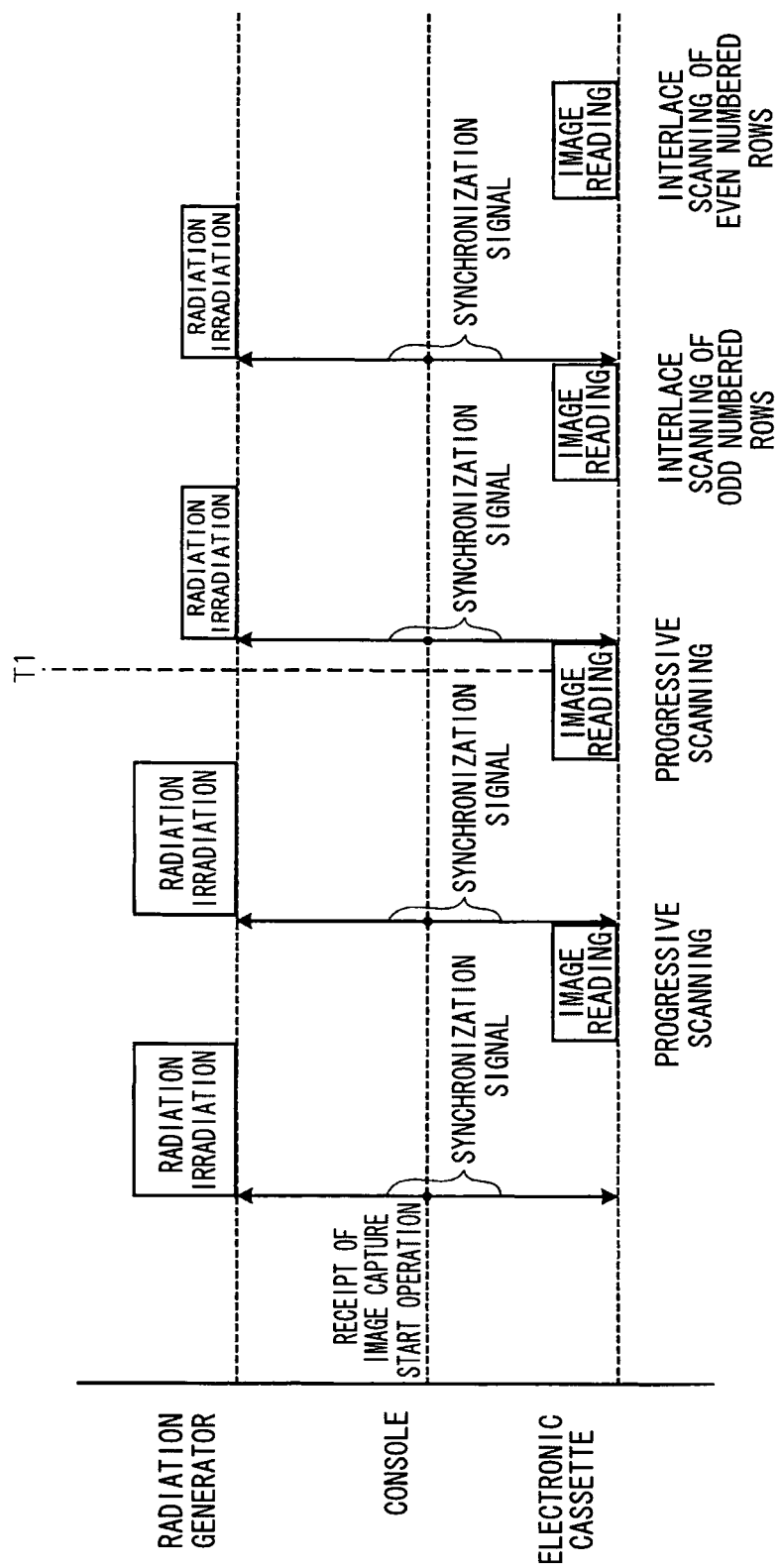
FIG. 15 is a timing chart showing a flow of image capture operation when the cumulative radiation amount irradiated from the radiation source has exceeded a permitted amount during fluoroscopic imaging by pulse irradiation according to the exemplary embodiment.

FIG. 14 shows a timing chart of image capture operation in a case in which the cumulative radiation amount irradiated from the radiation source 130 during fluoroscopic imaging by continuous irradiation has exceeded the permitted amount. FIG. 15 shows a timing chart of image capture operation in a case in which the cumulative radiation amount irradiated from the radiation source 130 during fluoroscopic imaging by pulse irradiation has exceeded the permitted amount.

As shown in FIG. 14 and FIG. 15, from the point in time T1, after the cumulative radiation amount irradiated from the radiation source 130 during fluoroscopic imaging has exceeded the permitted amount, the radiation amount per unit time for irradiation from the radiation source 130 is halved, and an interlace scanning method is adopted for the image reading mode in which the odd numbered rows and the even numbered rows are alternately read.

According to the exemplary embodiment, while the radiation amount irradiated from the radiation generator 34 is reduced to half, the reading cycle of the electrical charges of each of the pixels 74 connected to each of the gate lines 76 in both the odd numbered rows and the even numbered rows is doubled by adopting the interlace scanning method for image reading. Consequently, a reduction in quality of the radiographic images due to a reduction in radiation amount irradiated from the radiation generator 34 can be suppressed.

According to the exemplary embodiment, even though the reading cycle of the electrical charges in each of the pixels 74 is lengthened by performing image reading by the interlace scanning method, since the frame rate of fluoroscopic imaging is not reduced, missing an image at an important timing due to a reduction in the frame rate can be prevented.

Explanation has been given above of an exemplary embodiment of the present invention, however the scope of the present invention is not limited to that of the exemplary embodiment above. Various changes and improvements can be made to the above exemplary embodiment within a scope not departing from the spirit of the invention, and embodiments applied with these changes and improvements are included in the scope of the present invention.

The above exemplary embodiment does not intend to limit the invention according to the claims, and not all of the combination of features explained in the above exemplary embodiment are necessarily essential to the solution of the present invention. The above exemplary embodiment includes various levels of invention, and various inventions can be derived by appropriated combinations of the plural configuration elements disclosed. A number of the configuration elements can be removed from the total configuration elements shown in the exemplary embodiment, and as long as an effect is obtained, the configuration from which a number of configuration elements has been removed is derivable as an invention.

Explanation has been given in the exemplary embodiment above of cases of application to an electronic cassette that is a portable radiographic image capture apparatus. However, embodiments are not limited thereto, and application may also be made to a fixed installation radiographic image capture apparatus.

Furthermore, explanation has been given in the above exemplary embodiment, of a case in which a particular interlace scanning method is adopted as the image reading mode for reading the electrical charges that have been accumulated in each of the pixels 74 one line at a time when the radiation amount irradiated from the radiation generator 34 has been reduced. However, embodiments are not limited thereto, and, for example, interlace scanning method may be adopted that reads the electrical charges that have been accumulated in each of the pixels 74 every N lines (where N is an integer of 2 or above).

Explanation has been given in the above exemplary embodiment of a case in which the radiation amount irradiated from the radiation generator 34 is reduced by half (a multiple of ½), however embodiments are not limited thereto. For example, the radiation amount may be reduced to 1/M (where M is an integer of 2 or more) times the previous amount. N and M may differ from each other. In cases in which N=M, the sensitivity to radiation is substantially same to that when using a progressive scanning method. In cases in which N>M, the sensitivity to radiation is raised the larger N is than M, due to the increase in the radiation amount irradiated to each of the pixels 74.

An interlace scanning method may be adopted in which the gate lines 76 are divided into groups of L successive lines (wherein L is an integer of 2 or more) and reading is performed in turn for each of the groups.

Figure 16:
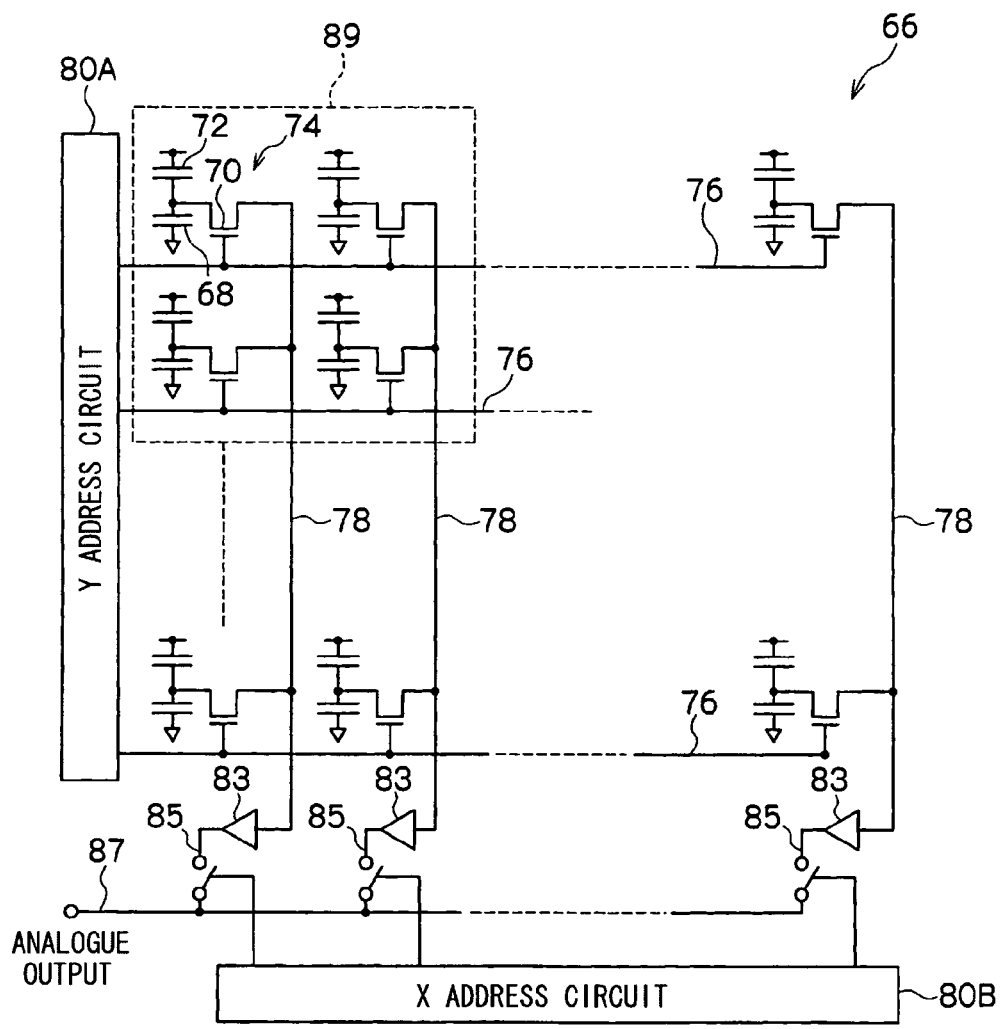
FIG. 16 is a plan view showing an example of a circuit configuration of a column reading type TFT active matrix substrate.

Explanation in the above exemplary embodiment is of a case in which the radiation detector 60 adopts a line reading method in which, plural gate lines 76 extend in a given direction (the row direction) of the TFT active matrix substrate 66 and the TFTs 70 of each of the pixels 74 along each of these gate lines 76 are switched ON or OFF. However, embodiments are not limited thereto. For example, as shown in FIG. 16, amps 83 and switches 85 may be provided at end portions of each of the data lines 78 of the TFT active matrix substrate 66, and each of the data lines 78 may be connected to read lines 87 through the amps 83 and the switches 85. In such a configuration, each of the individual gate lines 76 is connected to a Y address circuit 80A and each of the switches 85 is connected to an X address circuit 80B, thereby enabling each of the switches 85 to be switched ON or OFF from the X address circuit 80B. During reading, an ON signal is output from the Y address circuit 80A to the gate lines 76 according to the Y direction address of the pixels 74 to be read, and the switches 85 are switched ON from the X address circuit 80B according to the X direction address of the pixels 74 to be read, thereby reading out the electrical charges through the read lines 87. In a case in which the radiation detector 60 adopts a column reading method as described above, the pixels 74 may be divided into blocks 89 of plural adjacent pixels 74 (for example, 2×2 pixels), and electrical charges that have been accumulated in the pixels 74 may be read by each blocks 89 at one time for each image reading operation.

Explanation has been given in the above exemplary embodiment of cases in which the cumulative radiation amount irradiated from the radiation source 130 during fluoroscopic imaging is derived, and the image capture mode for fluoroscopic imaging is changed when the cumulative radiation amount has exceeded the permitted amount. However, embodiments are not limited thereto. For example, the cumulative irradiation duration irradiated from the radiation source 130 during fluoroscopic imaging may be derived, and the image capture mode for fluoroscopic imaging may be changed when the cumulative irradiation duration has exceeded a specific permitted irradiation duration. The permitted irradiation duration may be input to the operation panel 102 by an operator. Alternately, the permitted amount for irradiation for each image capture location may be pre-stored in the HDD 110 as image capture location specific permitted amount data, and in response to designation of the image capture location with the operation panel 102 by an operator, the permitted amount corresponding to the designated image capture location may be derived from the image capture location specific permitted amount data, the irradiation duration during fluoroscopic imaging until the cumulative radiation amount reaches the permitted amount may be estimated, and this estimated irradiation duration may be set as the permitted irradiation duration. In another embodiment, the exposure dose to a patient on a daily basis may be stored in the database 14A of the RIS server 14, the RIS server 14 may derive the exposure dose a patient is permitted to receive from the total value of exposure doses during a specific duration (such as the most recent 3 months period), notify the permitted exposure dose as the permitted amount to the console 42, and the console 42 may estimate the irradiation duration until the cumulative radiation amount during fluoroscopic imaging reaches the notified permitted amount, and set this estimated irradiation duration as the permitted irradiation duration.

Explanation has been given in the above exemplary embodiment of a case in which thinned reading is performed when the radiation amount irradiated from the radiation generator 34 has been reduced. Alternately, the gain of the operational amp 84A may be increased when the radiation amount irradiated from the radiation generator 34 is reduced. By increasing the gain of the operational amp 84A, the sensitivity to radiation raised in order that detection can be made even for cases in which the electrical charges that have been accumulated in each of the pixels 74 of the radiation detector 60 are small.

While explanation has been given in the above exemplary embodiment of a case in which the image capture method of fluoroscopic imaging is changed when the cumulative radiation amount irradiated from the radiation source 130 during fluoroscopic imaging has exceeded a permitted amount, the present invention is not limited thereto. For example, the operation panel 102 may be configured to receive instructions to change the reading mode, and during fluoroscopic imaging the reading method may be changed by an operator instructing changing of the reading method through the operation panel 102.

In this case, in a case in which an instruction to change the reading mode to interlace scanning is received, the console 42 may change, for example, the tube current in the exposure conditions designated at the fluoroscopic imaging start time to ½ the tube current, transmit the tube voltage designated at the fluoroscopic imaging start time and the changed tube current as the exposure conditions to the radiation generator 34 and the electronic cassette 32, and also transmits reading mode data designating interlace scanning method to the electronic cassette 32. Accordingly, the radiation amount per unit time for irradiation by the radiation source 130 is reduced to half, and the reading mode in the electronic cassette 32 is changed to interlace scanning method.

In a case in which an instruction to change the reading mode to progressive scanning is received, the console 42 transmits the tube voltage and the tube current that was designated at fluoroscopic imaging start time as the exposure conditions to the radiation generator 34 and the electronic cassette 32, and also transmits reading mode data designating a progressive scanning method to the electronic cassette 32. The radiation amount per unit time irradiated by the radiation source 130 is thereby returned to the initial radiation amount, and the reading mode of the electronic cassette 32 is changed to a progressive scanning method.

While explanation has been given in the above exemplary embodiment of a case in which the tube current is changed to ½ in order to reduce the radiation amount per unit time for irradiation from the radiation source 130 to ½, embodiments are is not limited thereto. For example, for cases of pulse irradiation, the irradiation period of each pulse irradiation may be shorted to half, so as to reduce the radiation amount. In case of pulse irradiation where plural times of pulse irradiation are performed for capturing each image (frame) in fluoroscopic imaging, the number of irradiation times for pulse irradiation may be reduced, so as to reduce the radiation amount. Further, the radiation amount may be reduced by adjusting combinations of radiation amount per unit time, irradiation period and number of times of irradiation for irradiation from the radiation source 130.

Figure 17:
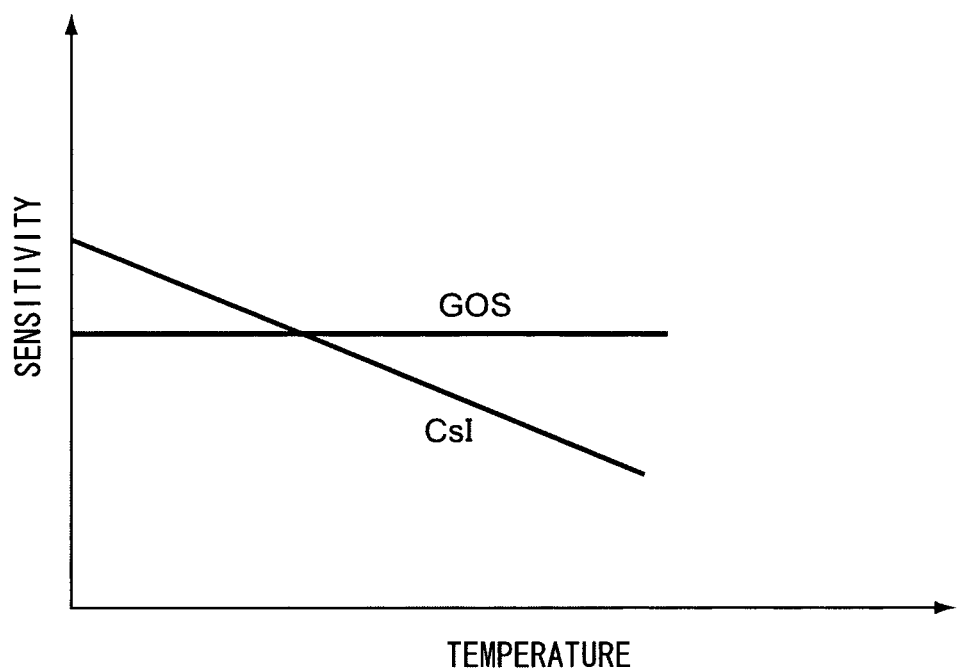
FIG. 17 is a graph showing the relationship between temperature and sensitivity of CsI and GOS.

Here, the CsI, which is used to form the scintillator 67, exhibits variation in sensitivity as shown in FIG. 17, and, for example, the sensitivity reduces about 0.3% by a temperature rise of 1° C. However, GOS hardly exhibits variation in sensitivity due to temperature change.

During image capture, various circuits and elements in the electronic cassette 32 such as the power source 96, gate line driver 80 and signal processor 82 generate heat. Particularly in video (motion) capture, the generated heat amount will be large since capturing time is relatively long. Therefore, the sensitivity of the scintillator 67 may be reduced in the electronic cassette 32 with the scintillator 67 formed by CsI due to the heat from the various circuits and elements during video capture. However, in the present exemplary embodiment, since the radiation amount is reduced and thinned reading is performed in which the reading period of charge in each of the pixels 74 is extended, the driving period of the gate line driver 80 and the signal processor 82 is reduced, which reduces the generated heat, whereby the reduction in sensitivity of the scintillator 67 can be controlled.

Figure 18:
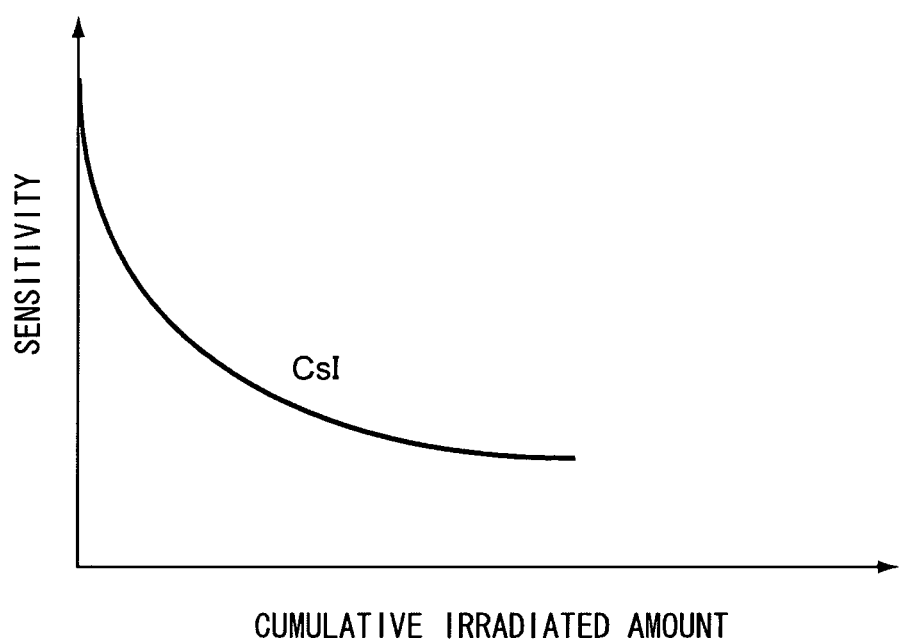
FIG. 18 is a graph showing the relationship between cumulative irradiated amount and sensitivity of CsI.

Further, as shown in FIG. 18, the sensitivity of CsI drops as the cumulative irradiated amount increases during performing of successive image capture, and recovers when a state of no radiation irradiation is maintained. Video capture may require a relatively long time, and if still image capture is frequently performed during the video capture, since the irradiation amount of radiation for still image capture is 10 to 1000 times that for one frame of video capture, the cumulative irradiated amount increases, and the sensitivity of the scintillator 67 is reduced. However, in the present exemplary embodiment, since the radiation amount is reduced and thinned reading is performed in which the reading period of charge in each of the pixels 74 is extended, a time of irradiating light from the scintillator 67 to the sensor portion 72 of each of the pixels 74 can be increased due to the extended reading period of charges in the pixels 74, whereby the reduction of sensitivity can be compensated for. As a result, there is no need to increase the radiation amount to be irradiated in order to maintain an image quality required for medical diagnosis, and an exposure amount with respect to a subject can be suppressed.

While explanation has been given in the above exemplary embodiment of cases in which a C arm is provided with the radiation generator 34, embodiments are not limited thereto. For example, a movable radiation generator without a C arm, such as disclosed in JP-A No. 2005-323673, may be used. A similar effect to that of the above exemplary embodiment can also be exhibited in such cases.

While the exemplary embodiment describes a case in which a movable device is applied as the radiation generator 34, embodiments are not limited thereto. For example, a radiation generator may be adopted in which only the radiation source 130 moves by way of a movement mechanism in the radiographic image capturing room 44.

While explanation has been given in the above exemplary embodiment of cases in which the electronic cassette 32 separately used without attached to the radiation generator 34, embodiments are not limited thereto. For example, the electronic cassette 32 may be used while being attached to the attachment structure 142 of the radiation generator 34. A similar effect to that of the above exemplary embodiment can also be exhibited in such cases.

In addition, the configuration of the RIS 10 (see FIG. 1), the configuration of the radiographic image capture room and the radiation generator 34 (see FIG. 2), the configuration of the electronic cassette 32 (see FIG. 3), and the configuration of the image capturing system 18 in the above exemplary embodiment are only examples thereof. Obviously non-required portions may be removed, new portions may be added, and connection configurations and the like can be changed within a scope not departing from the spirit of the present invention.

The flow of the fluoroscopic imaging changing processing program explained in the above exemplary embodiment (see FIG. 13) is also an example and obviously non-required steps may be removed, new steps may be added, and the processing sequence changed within a scope not departing from the spirit of the present invention.

What is claimed is:
1. A radiographic image capture system comprising:
a radiation detector including a plurality of pixels that generate electrical charges upon irradiation with radiation and that accumulate the electrical charges;
a radiation source that irradiates radiation onto the radiation detector;
a generator that reads the respective electrical charges that have been accumulated in each of the pixels as electrical signals and generates image data expressing a radiographic image based on the read electrical signals; and a controller that causes the generator to read the electrical charges that have been accumulated in each of the pixels at a specific frame rate in cases where continuous fluoroscopic imaging is performed to capture radiographic images, and, in a case in which a specific condition is satisfied, causes the radiation source to reduce the radiation amount being irradiated and causes the generator to perform thinned reading to read out the plurality of pixels one section at a time while extending the reading cycle of the electrical charges for each pixel.

2. The radiographic image capture system of claim 1, wherein the controller extends the reading cycle of the electrical charges for each of the pixels corresponding to an amount by which the radiation amount being irradiated is reduced.

3. The radiographic image capture system of claim 1, wherein in a case in which the specific condition is satisfied, the controller causes the radiation source to reduce the radiation amount for irradiation to 1/M, wherein M is an integer of 2 or above, times the previous value and causes the generator to perform thinned reading of the plurality of pixels one section at a time divided across N times, wherein N is an integer of M or above.

4. The radiographic image capture system of claim 1, wherein the method of thinned reading is an interlaced scanning method.

5. The radiographic image capture system of claim 1, wherein the controller causes the generator to perform thinned reading at the specific frame rate.

6. The radiographic image capture system of claim 1, wherein in a case in which the specific condition is satisfied, the controller reduces the radiation amount for irradiation by performing at least one of: reducing a radiation amount per unit time for irradiation, shortening the irradiation period in cases in which radiation is irradiated in a pulse mode, or reducing a number of times of irradiation in cases in which radiation is irradiated in a pulse mode.

7. The radiographic image capture system of claim 1, wherein:
the generator further comprises an amplifier that amplifies electrical signals read from the radiation detector; and
the controller increases the gain of the amplifier in a case in which the specific condition is satisfied.

8. The radiographic image capture system of claim 1, wherein:
the specific condition is that radiation has been irradiated from the radiation source in a specific permitted amount or for a specific permitted irradiation duration.

9. The radiographic image capture system of claim 1, further comprising:
a receiver that receives an instruction to change a reading mode, wherein the specific condition is that an instruction to change the reading mode has been received by the receiver.

10. The radiographic image capture system of claim 1, wherein the radiation detector is configured by stacking a fluorescent material layer that generates light due to being irradiated with radiation and a substrate on which a photoelectric conversion element is formed, the photoelectric conversion element converting the light generated by the fluorescent material layer into electric charge.

11. The radiographic image capture system of claim 10, wherein the fluorescent material layer includes CsI.

12. The radiographic image capture system of claim 10, wherein the radiation detector is configured to be irradiated with radiation from a side at which the substrate is disposed.

* * * * *